(12) United States Patent
Stougaard et al.

(10) Patent No.: US 8,288,143 B2
(45) Date of Patent: Oct. 16, 2012

(54) COLD-ACTIVE BETA-GALACTOSIDASE, A METHOD OF PRODUCING SAME AND USE OF SUCH ENZYME

(75) Inventors: Peter Stougaard, Kirke Hyllinge (DK); Mariane Schmidt, Frederiksberg (DK)

(73) Assignee: Kobenhavns Universitet, Copenhagen (DK)

( * ) Notice: Subject to any disclaimer, the term of this patent is extended or adjusted under 35 U.S.C. 154(b) by 0 days.

(21) Appl. No.: 13/148,853

(22) PCT Filed: Feb. 9, 2010

(86) PCT No.: PCT/EP2010/051596
§ 371 (c)(1),
(2), (4) Date: Sep. 20, 2011

(87) PCT Pub. No.: WO2010/092057
PCT Pub. Date: Aug. 19, 2010

(65) Prior Publication Data
US 2012/0058223 A1    Mar. 8, 2012

Related U.S. Application Data

(60) Provisional application No. 61/176,956, filed on May 11, 2009, provisional application No. 61/151,208, filed on Feb. 10, 2009.

(51) Int. Cl.
*C07K 1/00* (2006.01)
*C12N 9/38* (2006.01)
*C07H 21/04* (2006.01)
*C12N 15/00* (2006.01)
*C12N 1/20* (2006.01)

(52) U.S. Cl. .................. 435/207; 435/252.3; 435/320.1; 530/350; 536/23.2

(58) Field of Classification Search ............... 435/252.3, 435/320.1, 207; 530/350; 536/23.2
See application file for complete search history.

(56) References Cited

FOREIGN PATENT DOCUMENTS
WO    WO 01/04276    1/2001

OTHER PUBLICATIONS

Bialkowska et al., "A New β-Galactosidase with a Low Temperature Optimum Isolated from the Antarctic *Arthrobacter* sp.20B Gene Cloning, Purification and Characterization." *Arch Microbiol*, vol. 191, 2009, pp. 825-835.

Cieslinski et al., "Cloning, Expression, and Purification of a Recombinant Cold-Adapted β-Galactosidase from Antarctic Bacterium *Pseudoalteromonas* sp.22b." *Protein Expression & Purification*, vol. 39, 2005, pp. 27-34.

Coker et al., "Biochemical Characterization of a β-Galactosidase with a Low Temperature Optimum Obtained from an Antarctic *Arthrobacter* Isolate." *Journal of Bacteriology*, vol. 185, No. 18, Sep. 2003, pp. 5473-5482.

Coombs et al., "Biochemical and Phylogenetic Analyses of a Cold-Active β-Galactosidase from the Lactic Acid Bacterium *Carnobacterium piscicola* BA." *Applied and Environ. Microbiol.*, vol. 65, No. 12, Dec. 1999, pp. 5443-5450.

Fernandes et al., "β-Galactosidase from a Cold-Adapted Bacterium: Purification, Characterization and Application for Lactose Hydrolysis." *Appl. Microbiol. Biotechnol.*, vol. 58, 2002, pp. 313-321.

Hildebrandt et al., "A New Cold-Adapted β-D-Galactosidase from the Antarctic *Arthrobacter* sp. 32-Gene Cloning, Overexpression, Purification and Properties." *BMC Microbiology*, vol. 9, No. 151, 2009, 11 pages.

Hu et al., "Molecular Cloning and Characterization of the Gene Encoding Cold-Active β-Galactosidase from a Psychrotrophic and Halotolerant *Planococcus* sp. L4." *J. Agric. Food Chem.*, vol. 55, 2007, pp. 2217-2224.

Nakagawa et al., "Isolation and Characterization of Psychrophiles Producing Cold-Active β-Galactosidase." *Letters in Applied Microbiology*, vol. 37, 2003, pp. 154-157.

Nakagawa et al., "Cold-Active Acid β-Galactosidase Activity of Isolated Psychrophilic-Basidiomycetous Yeast *Guehomyces pullulans*." *Microbiological Research*, vol. 161, 2006, pp. 75-79.

Nakagawa et al., "Purification and Molecular Characterization of Cold-Active β-Galactosidase from *Arthrobacter psychrolactophilus* Strain F2." *Appl. Microbiol. Biotechnol.*, vol. 72, 2006, pp. 720-725.

Sorensen et al., "Secreted β-galactosidase from a *Flavobacterium* sp. Isolated from a Low-Temperature Environment." *Appl. Microbiol. Biotechnol*, vol. 70, 2006, pp. 548-557.

Trimbur et al., "Characterization of a Psychrotrophic *Arthrobacter* Gene and Its Cold-Active β-Galactosidase." *Applied and Environ. Microbiol.*, vol. 60, No. 12, 1994, pp. 4544-4552.

Turkiewicz et al., "Antarctic Marine Bacterium *Pseudoalteromonas* sp. 22b as a Source of Cold-Adapted β-Galactosidase." *Biomolecular Engineering*, vol. 20, 2003, pp. 317-324.

"*Alkalilactibacillus ikkense* strain 517 beta-galactosidase gene, partial cds." XP002579363, Retrieved from EM_Pro:FJ811841, Database Accession No. FJ811841, Apr. 23, 2010, 2 pages.

International Search Report for Application No. PCT/EP2010/051596 mailed May 18, 2010.

*Primary Examiner* — Maryam Monshipouri
(74) *Attorney, Agent, or Firm* — Merchant & Gould P.C.

(57) ABSTRACT

A novel cold-active beta-galactosidase is enzyme specific for lactose. The enzyme is thus useful in e.g. the food industry for catalyzing at low temperatures the hydrolysis of lactose disaccharide into its constituent monosaccharides, glucose and galactose. A method produces the cold-active beta-galactosidase by recombinant DNA technology.

23 Claims, 17 Drawing Sheets

COLD-ACTIVE BETA-GALACTOSIDASE, A METHOD OF PRODUCING SAME AND USE OF SUCH ENZYME

This application is a National Stage Application of PCT/EP2010/051596, filed 9 Feb. 2010, which claims benefit of Ser. No. 61/176,956, filed 11 May 2009 in the United States, and which also claims benefit of Ser. No. 61/151,208, filed 10 Feb. 2009 in the United States, and which applications are incorporated herein by reference. To the extent appropriate, a claim of priority is made to each of the above disclosed applications.

FIELD OF THE INVENTION

The present invention relates to a novel cold-active beta-galactosidase enzyme specific for lactose. The enzyme is thus useful in e.g. the food industry for catalyzing at low temperatures the hydrolysis of lactose disaccharide into its constituent monosaccharides, glucose and galactose. The present invention further provides a method of producing the cold-active beta-galactosidase by recombinant DNA technology.

BACKGROUND OF THE INVENTION

Beta-galactosidase (beta-D-galactoside galactohydrolase, EC 3.2.1.23) is an enzyme capable of hydrolyzing the disaccharide lactose to its monosaccharide constituents, D-glucose and D-galactose. Beta-galactosidases are found in a large variety of organisms, like mammals, plants, fungi, yeasts, and bacteria. In Nature, beta-galactosidases hydrolyze lactose and other D-galactose-containing carbohydrates. In the industry, beta-galactosidases have been used primarily within the food industry. Beta-galactosidase hydrolysis of lactose and lactose-containing dairy products are used throughout in the dairy industry in the preparation of lactose-free or low-lactose products, which may be consumed by humans suffering from lactose intolerance. Hydrolysis of lactose by beta-galactosidases may also be used in applications where the removal of lactose is required, i.e. prevention of crystallisation of lactose in food and removal of D-galactose moieties in glycosylated proteins. Other applications of beta-galactosidases comprise hydrolysis of lactose into D-galactose and D-glucose with the subsequent modification of the monosaccharides to high value products, like the sweetener D-tagatose (Jorgensen et al. 2004).

Application of beta-galactosidases could be used to produce lactose-free and low-lactose dairy products for lactose intolerant humans.

The major applications for lactose hydrolysis are listed below.
a) Liquid milk. Lactose hydrolysis in liquid milk improves digestibility for lactose intolerant consumers. In flavoured milks, lactose hydrolysis increases sweetness and enhances flavours.
b) Milk powders. Lactose hydrolysed milk powders for dietetic uses, especially for infants with temporary beta-galactosidase deficiency.
c) Fermented milk products. In some cases, lactose hydrolysis in milk used for the manufacture of cheese and yoghurt can increase the rate of acid development and thus reduce processing time.
d) Concentrated milk products. Lactose hydrolysis in concentrated milk products (e.g. sweetened condensed milk, ice cream) prevents crystallisation of lactose.
e) Whey for animal feed. Lactose hydrolysis in whey enables more whey solids to be fed to pigs and cattle and also prevents crystallisation in whey concentrate.
f) Whey. Lactose hydrolysed whey is concentrated to produce a syrup containing 70-75 percent solids. This syrup provides a source of functional whey protein and sweet carbohydrate and is used as a food ingredient in ice cream, bakery and confectionery products.

The conventional approach in food processing is to carry out the hydrolysis of lactose at 40° C. during approximately four hours.

However, milk or lactose solution as a raw material is a preferable nutrition source for bacteria. As the result, the putrefaction owing to the saprophyte contamination during the treatment is a serious problem in the food production. Thus, the fact is that the conventional beta-galactosidase is of limited use.

Most beta-galactosidases in practical use are active only at temperatures above 20-30° C., temperatures where food spoiling bacteria thrive at best.

Attempts to use thermophilic beta-galactosidases have been used but the products have suffered from off flavours and reduced organoleptic properties due to the heat treatment, and the processes have demanded high energetic costs.

A number of cold-active beta-galactosidases have been described from *Arthrobacter* (Coker, et al. 2003; Karasová-Lipovová, et al. 2003; Nakagawa et al. 2003; Nakagawa et al. 2006), from *Carnobacterium piscicola* (Coombs and Brenchley, 1999) and from *Pseudoalteromonas* (Cieslinski, et al. 2005; Fernandes, et al. 2002; Hoyoux, et al. 2001; Turkiewicz, et al. 2003). Furthermore, Nakagawa et al. (2006) described a cold-active beta-galactosidase from the yeast *Guehomyces pullulans*. However, the activity of cold-active beta-galactosidases described so far is low at the low temperatures, which is wanted by the dairy industry. The beta-galactosidase from the yeast *Guehomyces pullulans* had approximately 17% at 0° C. (Nakagawa et al. 2005), the beta-galactosidases from *Carnobacterium piscicola* BA showed approximately 24% activity at 10° C. (Coombs and Brenchley, 1999) and the enzymes from *Pseudoalteromonas* isolates showed 39% activity (Fernandes et al. 2002), 22% activity (Cieslinski et al. 2005), and 12% activity (Hoyoux et al. 2001) at 10° C. So far, the beta-galactosidases with highest activity at low temperatures have been isolated from Antarctic *Arthrobacter* isolates. Karasová-Lipovová, et al. (2003) showed that a psychrotolerant *Arthrobacter* sp. C2-2 isolate produced beta-galactosidase, which displayed 19% of its maximal activity at 10° C., Coker et al. (2003) described an enzyme from an Antarctic *Arthrobacter* isolate with approximately 50% at 0° C., and Nakagawa et al. (2003, 2006) described a beta-galactosidase from *A. psychrolactophilus* F2, which had its temperature optimum at 10° C.

However, the cold-active beta-galactosidase from the Antarctic *Arthrobacter* was produced in low amounts in native cells and attempts to produce the enzyme recombinantly in *E. coli* were unsuccessful since about 90% of the enzyme was located in insoluble inclusion bodies (Coker et al. 2003). The cold-active beta-galactosidase from *A. psychrolactophilus* F2 could be produced heterologously, but had lower activity than the other *Arthrobacter* beta-galactosidases (Nakagawa et al. 2006).

Therefore, in order to develop a low-temperature process for hydrolysis of lactose there is a need for a novel cold-active beta-galactosidase and a method for producing such enzyme.

SUMMARY OF THE INVENTION

The present invention has, by using recombinant DNA technology, for the first time made it possible to provide a cold-active beta-galactosidase with high specific activity in industrially appropriate quantities for the manufacturing of food products and pharmaceuticals.

Accordingly, the present invention provides a purified cold-active beta-galactosidase, specific for lactose, having a stable enzymatic activity at temperatures less than 8° C., and specifically at 4° C., which corresponds to refrigerating conservation temperature for dairy products. The enzyme of the present invention is consequently able to hydrolyse lactose in dairy products and milk processing at such a low temperature that saprophytes are hindered to proliferate. The hydrolysis of lactose can be carried out in these refrigeration conditions with no need of a particular treatment to the dairy product concerned.

Specifically, the present invention provides a cold active beta-galactosidase having the sequence as defined in SEQ ID NO. 1, or one having at least 80% homology to the amino acid sequence as defined in SEQ ID NO. 1, the amino acid sequence being selected so that the enzyme has a stable enzymatic activity at temperatures less than 8° C. Preferably the amino acid sequence has at least 90%, and more preferably 95%, homology to the amino acid sequence as defined in SEQ ID NO. 1.

In order to obtain the cold-active beta-galactosidase of the present invention there is further provided a DNA sequence, which
 a) encodes a protein with an amino acid sequence as given in SEQ ID NO. 1, or
 b) hybridises under stringent or very stringent conditions to the sequence of a), or
 c) is degenerative of the sequence of a) or b)

Preferably the DNA sequence is derived from the genus *Alkalilactibacillus*, such as the species *Alkalilactibacillus ikkense*, and has a nucleotide sequence as given in SEQ ID NO. 2.

In a further embodiment, the present invention provides a recombinant vector comprising a DNA sequence that encodes a protein with an amino acid sequence as given in SEQ ID NO. 1, or one having at least 80% homology to the amino acid sequence as defined in SEQ ID NO. 1, the amino acid sequence being selected so that the enzyme has a stable enzymatic activity at temperatures less than 8° C. Preferably the amino acid sequence has at least 90%, and more preferably 95%, homology to the amino acid sequence as defined in SEQ ID NO. 1.

Another object of the present invention is a strain of an isolated *Alkalilactibacillus* bacterium capable of producing a cold-active beta-galactosidase according to the present invention. A preferable strain is *Alkalilactibacillus ikkense* deposited on the 3rd of Mar., 2009, under the Budapest Treaty at the BCCM/LMG-Collection (Belgian Coordinated Collections of Microorganisms) with the Accession No LMG P-24866 and variants and mutants derived therefrom.

To purify the cold-active beta-galactosidase according to the present invention, a bacterium living in the Greenland area was isolated and characterised in order to study how its enzymes, and particularly, the beta-galactosidase was adapted to cold. These studies led to the purification of the beta-galactosidase, meaning that this protein was obtained substantially free of other proteins using protein purification steps known in the art.

Thus, another object of the present invention is a strain of an isolated *Alkalilactibacillus* bacterium capable of producing a cold-active beta-galactosidase according to the present invention. A preferable strain is *alkalilactibacillus ikkense*.

Another object of the invention is a recombinant plasmid or vector suited for transformation of a host, capable of directing the expression of a DNA sequence according to the invention in such a manner that the host expresses the cold-active beta-galactosidase of the present invention in recoverable form.

According to the invention, another object is the so transformed host. A variety of host-expression systems may be conceived to express the cold-active beta-galactosidase coding sequence, for example bacteria, yeast, insect cells, plant cells, mammalian cells, etc. Particularly, in yeast and in bacteria, a number of vectors containing constitutive or inducible promoters may be used.

It is also an object of the present invention to provide a process for purifying the cold-active beta-galactosidase according to the present invention from a bacterium as well as to provide a process for producing cold-active beta-galactosidase according to the invention in a transformed host.

Accordingly, the invention pertains to a method of producing a polypeptide having cold-active beta-galactosidase activity, comprising isolating a DNA fragment encoding the polypeptide, inserting said DNA fragment into an appropriate host organism, cultivating the host organism under conditions, which lead to expression of the a polypeptide with cold-active beta-galactosidase activity and recovering said polypeptide from the cultivation medium or the host organism.

An appropriate host organism is preferably selected from the group consisting of *Escherichia, Bacillus, Bifidobacterium, Lactococcus, Lactobacillus, Streptomyces, Leuconostoc, Streptomyces, Saccharomyces, Kluyveromyces, Candida, Torula, Torulopsis* and *Aspergillus*.

In a further aspect, the invention relates to a recombinant DNA molecule comprising a DNA fragment encoding a polypeptide having cold-active beta-galactosidase activity and to a microbial cell comprising such recombinant DNA molecule.

In another aspect, the invention pertains to the use of the above polypeptide with cold-active beta-galactosidase activity or a microbial cell expressing such polypeptide in the manufacturing of a food product or a pharmaceutical product.

In another useful aspect, there is provided a method for reducing the lactose content of a food product, comprising adding to the food product an amount of the polypeptide or the microbial cell as disclosed herein, which is sufficient to remove at least part of the lactose present in said food product.

In a practical aspect, the invention pertains to the inactivation of the beta-galactosidase activity of the polypeptide by a moderate increase of the temperature.

In a further interesting aspect, there is provided a method using the polypeptide harbouring a cold-active beta-galactosidase activity or a microbial cell according to the invention in the hydrolysis of lactose, whereby the polypeptide and/or the microbial cell is applied to a reactor containing lactose, which is hydrolyzed under low-temperature conditions.

These and other objects of the present invention will be apparent from the following disclosure.

Other characteristics of the present invention are listed in the annexed claims.

DETAILED DESCRIPTION OF THE INVENTION

"Beta-galactosidase" (beta-D-galactoside galactohydrolase, EC 3.2.1.23) is defined as an enzyme capable of hydrolysing lactose to the monosaccharides D-glucose and D-galactose.

"Cold-active" is defined as having activity at temperatures at 15° C. and below, preferably at 10° C. and below and most preferably at 5° C. and below.

A "host cell" is selected from a group of microorganisms comprising fungi, yeasts, and prokaryotes. The microorganism is more preferably a prokaryote and most preferably a bacterium.

Conditions of incubating beta-galactosidase with lactose are defined by performing incubation at a temperature between 0° C. and 20° C., preferably between 5° C. and 15° C.

The term "stringent condition" refers to a condition such that a hybridization is conducted in a solution containing 6×SSC (20×SSC represents 333 mM Sodium citrate, 333 mM NaCl), 0.5% SDS and 50% formamide at 42° C., and then the hybridized products are washed in a solution of 0.1×SSC, 0.5% SDS at 68° C., or to conditions as described in Nakayama, et al., Bio-Jikken-Illustrated, vol. 2, "Idenshi-Kaiseki-No-Kiso (A Basis for Gene Analysis)", pp. 148-151, Shujunsha, 1995.

EXAMPLES

Example 1

Isolation of Bacteria Producing Cold-Active Beta-Galactosidases 1.1 Sampling of Bacteria Ikaite material was collected by scuba divers in the Ikka Fjord, South West Greenland (61° 11'N, 48° 01'W) from a depth of approximately six to ten meters. The columns were between 36-70 cm in length and between 5 and 30 cm in diameter. The columns were kept cold during transportation to the field laboratory.

1.2 Screening Bacteria for Beta-Galactosidase Production

Approximately 3 cm$^3$ of ikaite material from a slice 15-18 cm from the top of an ikaite column was drilled out and suspended in 250 ml R2 broth (Schmidt et al. 2006) buffered to pH 10 with 0.2 M Na$_2$CO$_3$/NaHCO$_3$ buffers as described by Stoll and Blanchard (1990). After incubation at 5° C. for 2 months the culture was inoculated onto R2 medium, pH 10 without glucose but supplemented with lactose (1% w/v), 5-bromo-4-chloro-3-indolyl-β-D-galactopyranoside (X-gal) (40 µg/ml), 10 mM isopropyl-beta-D-thiogalactopyranoside (IPTG) and agar (1.5%, w/v). The plates were incubated at 5° C. for one to two weeks. A total of 17 blue colonies indicating production of beta-galactosidase were detected. Since 16S rRNA gene analyses of the seventeen isolates showed identical sequences only one of the isolates, strain 517, was chosen for further characterization.

Example 2

Taxonomical Analysis of Isolate 517 and Description of a New Genus and Species, *Alkalilactibacillus Ikkense*

2.1 Phylogenetic Analysis of 16S rRNA Gene Sequences

Figure 1:
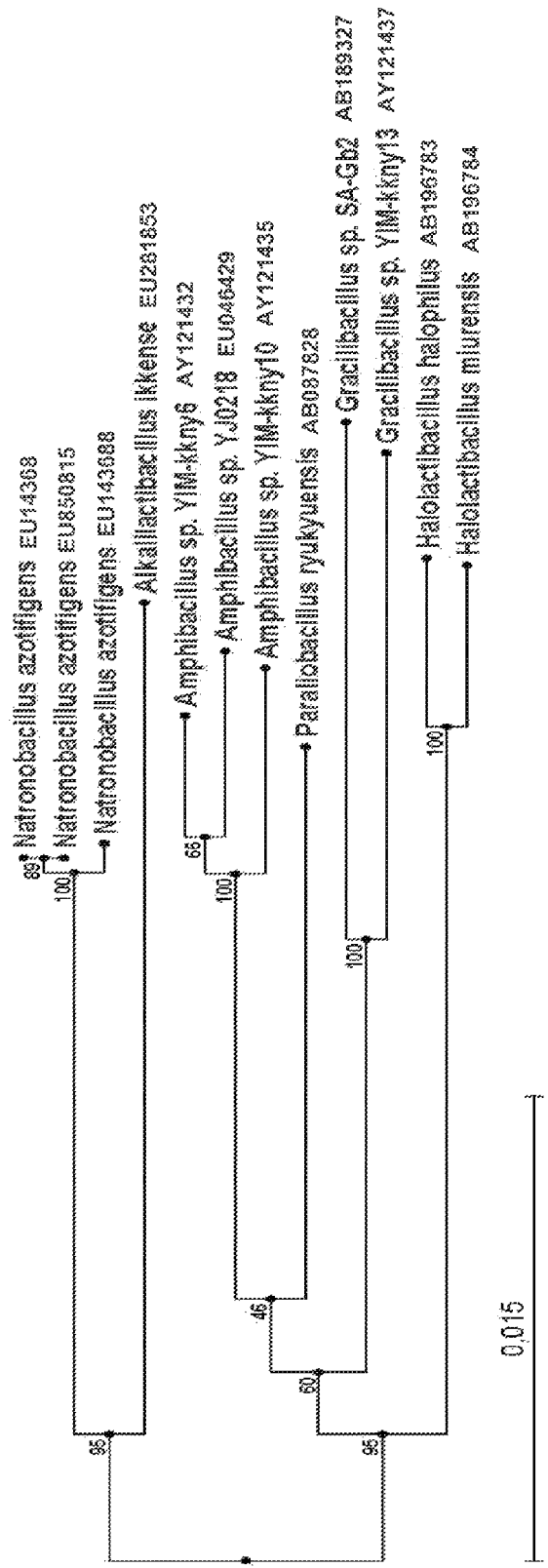
FIG. 1 discloses a phylogenetic tree of 16S rRNA gene sequences from *Alkalilactibacillus ikkense* strain 517 and its closest relatives within the rRNA group 1 in the phyletic assemblage classically defined as the genus *Bacillus*. Bootstrap (n=100) values are shown. Bar, 0.015 substitutions per nucleotide position.

DNA for phylogenetic analysis was extracted from cells of isolate 517 using FastDNA SPIN Kit for Soil as described by the manufacturer (BIO 101, Irvine, Calif.). 16S rRNA gene amplification was carried out using the primers 27F and 1492R (Lane 1991), and DNA sequencing was carried out at MWG Biotech AG (Ebersberg, Germany) using the same two primers plus additional primers 519R, 532F, 907F, and 907R (Lane 1991). The near full length DNA sequence of the 16S rRNA gene from isolate 517 was submitted to GenBank/EMBL/DDBJ with the accession number EU281853. Related sequences were retrieved from public databases using BLASTn at the NCBI server (http://www.ncbi.nlm.nih.gov/blast/). The closest related 16S rRNA gene sequences were aligned using the Clustal W multiple alignment program MegAlign 5.03 (DNASTAR, Inc., Madison, Wis.). The Clustal W analysis showed that the closest relatives were *Natronobacillus azotifigens* (accession no. EU850815) (Sorokin et al. 2008), *Paraliobacillus ryukyuensis* (accession no. AB087828) (Ishikawa et al. 2002), *Halolactibacillus halophiles* (accession no. AB196783) (Ishikawa et al. 2005), *Halolactibacillus miurensis* (accession no. AB196784) (Ishikawa et al. 2005), *Amphibacillus tropicus* (accession no. AF418602) (Zhilina et al. 2001, 2002), and *Gracilibacillus halotolerans* (accession no. AF036922) (Wainø et al. 1999). Isolate 517 was most closely related to *N. azotifigens, P. ryukyuensis* and *A. tropicus* with 95.9%, 94.4% and 93.9% sequence similarity, respectively. The sequence similarity between isolate 517 and both *H. halophiles, H. miurensis*, and *G. halotolerans* was 93.4%. Thus, the distance in 16S rRNA gene sequence similarity between isolate 517 and the closest related is below the 97% similarity, which is often used as a preliminary guideline for species separation. A phylogenetic tree was created by neighbour-joining analysis (bootstrap=100) using TREECON 1.3b software (Van de Peer and De Wachter, R. 1994) FIG. 1.

2.2 DNA-DNA Hybridization and Base Composition Analysis of Genomic DNA

DNA-DNA hybridization and DNA base composition (G+C content) was carried out at DSMZ (Braunschweig, Germany). DNA was isolated using a French pressure cell (Thermo Spectronic) and was purified by chromatography on hydroxyapatite as described by Cashion et al. (1977). DNA-DNA hybridization was carried out as described by De Ley et al. (1970) under consideration of the modifications described by Huss et al. (1983) using a model Cary 100 Bio UV/VIS-spectrophotometer equipped with a Peltier-thermostatted 6×6 multicell changer and a temperature controller with in-situ temperature probe (Varian). DNA-DNA hybridization between isolate 517 and the closest related based on 16S rRNA sequence similarity *P. ryukyuensis* was 28.8%, and between isolate 517 and *H. miurensis* it was 24.7%.

For determination of GC content, the DNA was hydrolyzed with P1 nuclease and the nucleotides dephosphorylated with bovine alkaline phosphatase (Mesbah et al. 1989). The resulting deoxyribonucleotides were analyzed by HPLC. The DNA G+C content of isolate 517 was 38.4 mol %, which is fairly similar to the closest related species. The G+C content of *N. azotifigens* is 36.1-38.5 mol % (Sorokin et al. 2008), *H. halophiles* and *H. miurensis* is reported to be 38.5-40.7 mol % (Ishikawa et al. 2005), for *P. ryukyuensis* it is 35.6 mol % (Ishikawa et al. 2002), and for *G. halotolerans* it is reported to be 38 mol % (Wainø et al. 1999).

The phylogenetic results and data on GC content indicate that isolate 517 represent a new species within a new genus, since the threshold value for DNA-DNA hybridization to separate two species is 70% (Wayne et al., 1987). Thus, we propose that isolate 517 represents a new genus *Alkalilactibacillus* gen. nov. comprising the species *Alkalilactibacillus ikkense* sp. nov.

Example 3

Characterization of Native Ikka-Beta-Galactosidase from *Alkalilactobacillus ikkense*

3.1 Beta-Galactosidase Assay.

Beta-galactosidase activity was assayed by hydrolysis of o-nitrophenyl-beta-D-galactopyranoside (ONPG) and measuring the absorbancy of the released o-nitrophenyl (ONP) compound in a spectrophotometer at 415 nm. In the assay, the release of ONP from 1 mM ONPG by the recombinant beta-galactosidase activity was measured at 415 nm at 20° C. and pH 7.0 (0.1 M NaH$_2$PO$_4$/Na$_2$HPO$_4$). The reactions were stopped by adding 300 µl 0.6 M Na$_2$CO$_3$. Assays were performed at 0, 5, 10, 20, 30, 40, 50, and 60° C. for 30 minutes. The sodium phosphate buffers were pre-heated to the respective temperatures prior to assay start.

Thermostability analysis of the enzyme was carried out by placing an aliquot of enzyme at temperatures 0, 10, 20, 30, 40, and 50° C. and taking samples at t=0 to t=24 hours. Immediately after taking the samples, they were cooled and assayed at 20° C. as described above.

The pH activity profile was studied using a mixed pH buffer (250 mM Tris, 250 mM MES, 250 mM acetic acid)

adjusted from pH 4 to pH 10 with HCl or NaOH. The samples were incubated at 20° C. for 1 hour and assayed as described above.

3.2 Production of Native Ikka-Beta-Galactosidase.

*Alkalilactibacillus ikkense* cells were cultivated in liquid R2 medium supplemented with lactose and IPTG at 15° C. for 3 days on a rotary shaker. Cells were harvested by centrifugation in a Sigma® 3-18M centrifuge at 4,700 rpm and the pellet was resuspended in 2 ml of 0.1 M $NaH_2PO_4/Na_2HPO_4$, pH 7. Cells were lysed by bead beating in a FastPrep FP120 instrument (Bio101/Savant) for 3 times 25 sec at speed 5.5. The supernatant was then removed from the glass beads and centrifuged for 15 min at 10,000*g at 4° C. The cell free supernatant was then used for assaying.

3.3 Characterization of Temperature Optimum of Native Ikka-Beta-Galactosidase.

Figure 2:
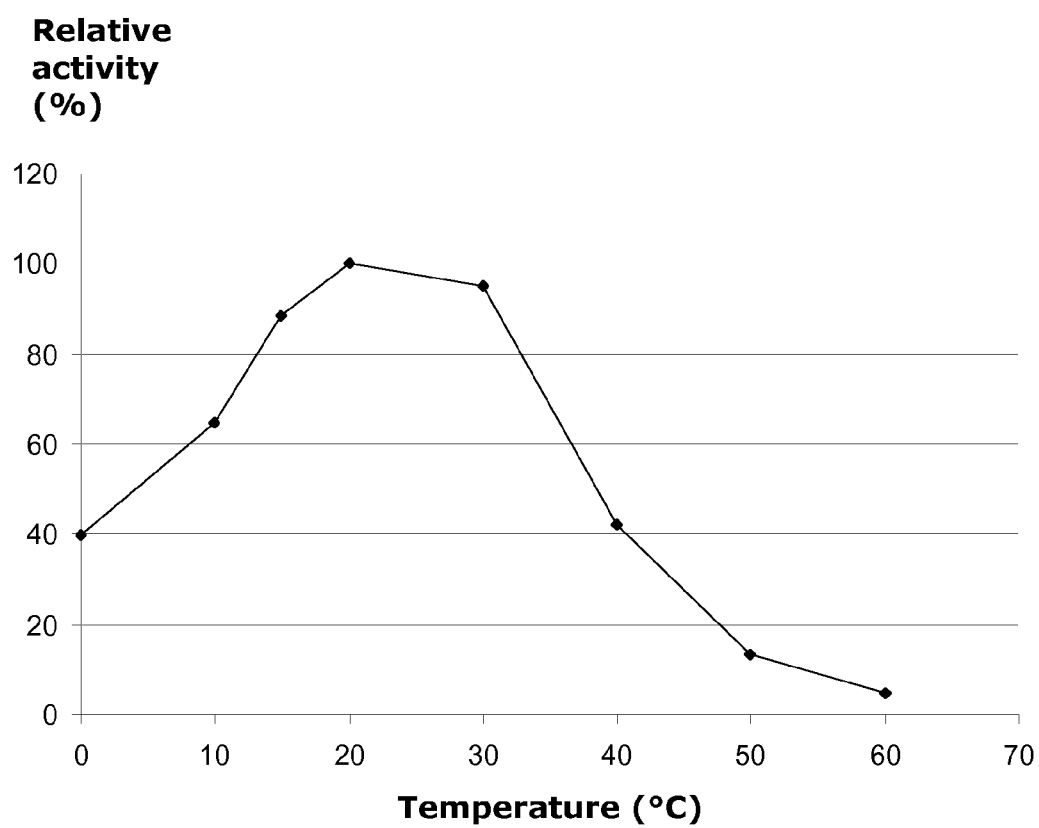
FIG. 2 shows temperature dependence of native Ikka-beta-galactosidase. Y-axis is the relative activity in percent of the maximal activity. X-axis is the incubation temperature.

The native Ikka-beta-galactosidase displayed maximal activity at 20° C., 40% of the maximal activity was obtained at 0° C., and more than 60% of the maximal activity was observed at 10° C. (FIG. 2). Above 30° C. the enzyme was only moderately active and virtually no activity was observed at 60° C.

Figure 3:
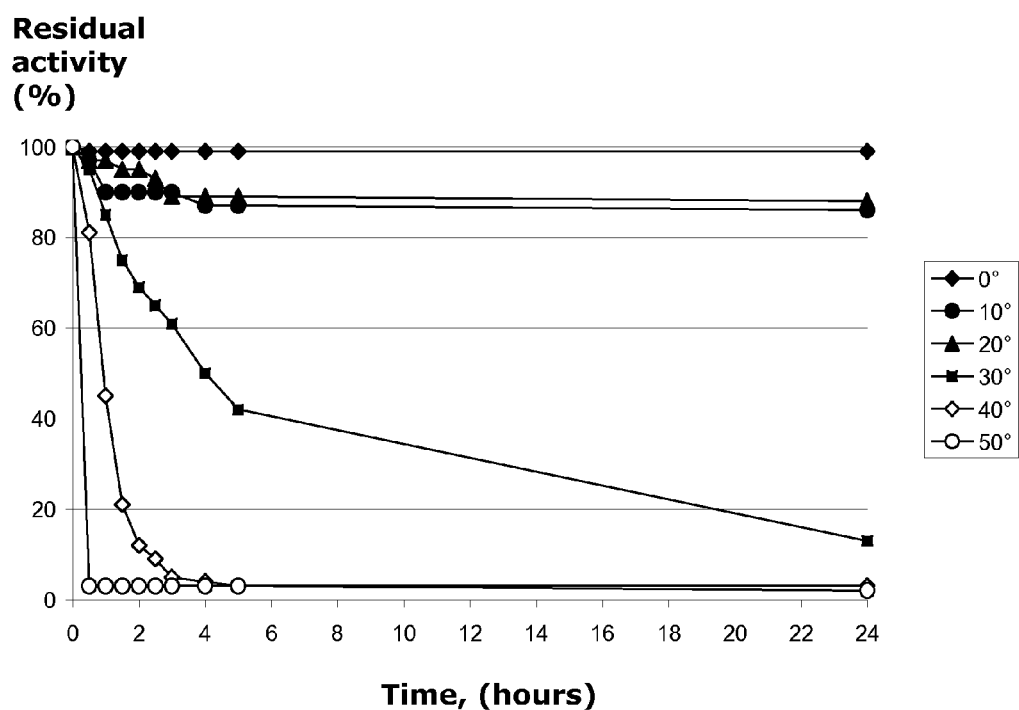
FIG. 3 shows temperature stability of native Ikka-beta-galactosidase. Y-axis is the residual activity left after incubation at the time indicated on the X-axis. ♦, ●, ▲, ■, ◊, ○, indicate incubation temperatures at 0, 10, 20, 30, 40, and 50° C., respectively.

The temperature stability of the Ikka-beta-galactosidase was investigated. FIG. 3 shows that almost 100% of the residual activity was observed after 24 hours incubation at 0° C. and that more than 80% activity was left after 24 hours at 20° C. At temperatures above 20° C., the native Ikka-beta-galactosidase rapidly lost activity (FIG. 3). The inactivation at high temperatures was shown to be irreversible.

Figure 4:
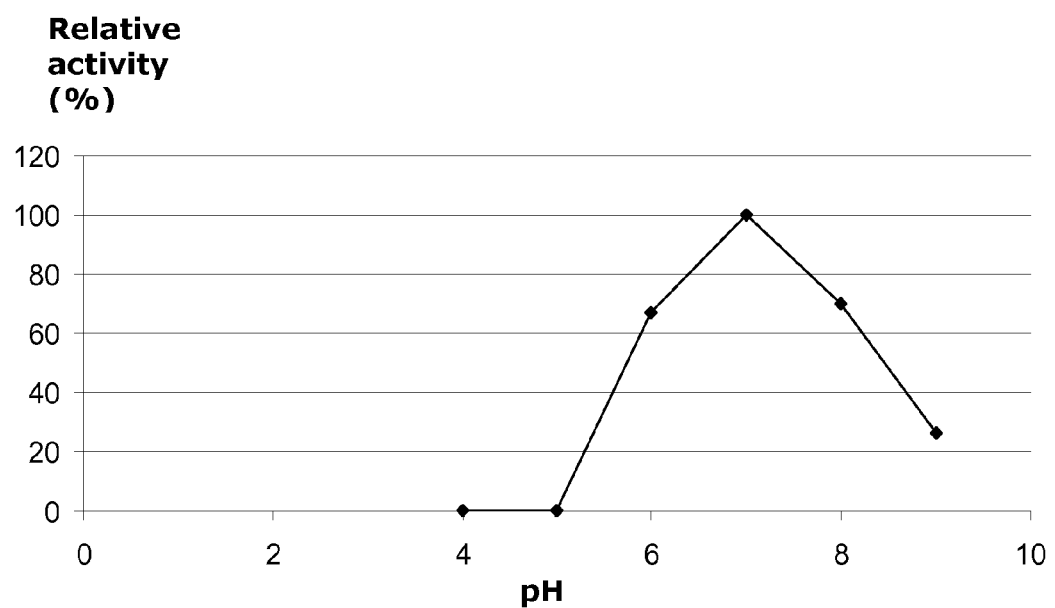
FIG. 4 discloses pH dependence of native Ikka-beta-galactosidase. Y-axis is the relative activity in percent of the maximal activity. X-axis is pH in the beta-galactosidase assay.

The pH dependence of the native Ikka-beta-galactosidase was investigated. FIG. 4 shows that maximal activity of the native Ikka-beta-galactosidase was observed at pH 7, and that the enzyme displayed approximately 70% of the maximal activity at pH 6 and at pH 8. At pH 9, approximately 25% of maximal activity was observed. The enzyme showed no activity at pH 5 and below or at pH 10 and above (FIG. 4).

3.4 SDS-PAGE of Native Ikka-Beta-Galactosidase.

Figure 5:
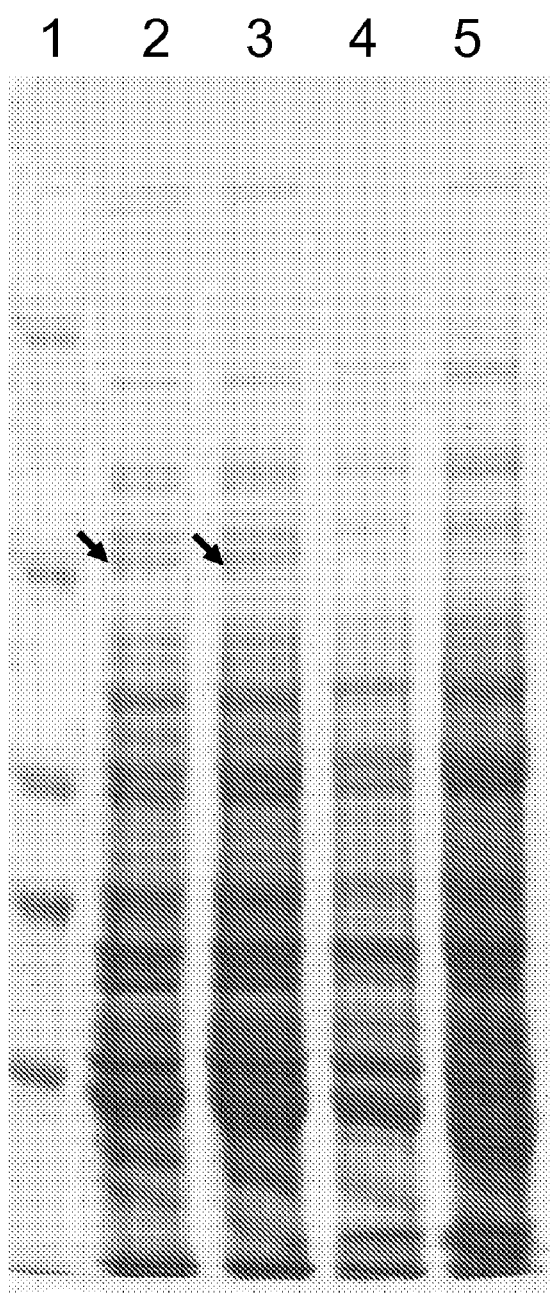
FIG. 5 shows SDS-PAGE of extracts from native *A. ikkense* cells induced with 1 mM IPTG (lanes 2 and 3) and from uninduced, native *A. ikkense* (lanes 4 and 5). Arrows in lanes 2 and 3 indicate the 120 kDa beta-galactosidase band. Lane 1 is molecular weight marker. The marker at 120 kDa is beta-galactosidase from *E. coli*.

Extracts from cells of *A. ikkense* induced with 1 mM IPTG and uninduced were analysed in SDS-PAGE (sodium dodecyl sulfate-polyacrylamide gel electrophoresis) (FIG. 5). Intracellular extracts were prepared by lysing the cells using bead-beating as described above in 3.2. The extracts (0.5-5 µl) were mixed with 12.5 µl 4*LDS sample buffer, 5 µl 10*DTT and 0.1 M $NaH_2PO_4/Na_2HPO_4$ to a final volume of 50 µl. The samples were heated to 70° C. for 10 minutes and 30 µl was loaded onto a 4-12% SDS gel. The gel was run in a XCell SureLoce™ Mini-Cell (Invitrogen, CA, USA) at 150 V for 1 hour at room temperature. After electrophoresis, the gel was stained using Coomassie Brilliant Blue R-250 (0.1% Coomassie Brilliant Blue R-250 (Serva, Heidelberg, Germany) in 40% EtOH and 10% acetic acid). FIG. 5 shows that a strong 120 kDa band was observed in the lanes with extracts from *A. ikkense* cells induced with IPTG and that this band was missing in lanes with extracts from non-induced cells. Thus, the 120 kDa band was assumed to be the native Ikka-beta-galactosidase.

Example 4

Isolation and Characterization of the Ikka-Beta-Galactosidase Gene from *Alkalilactobacillus Ikkense*

4.1 Isolation of the Ikka-Beta-Galactosidase Gene

DNA from *A. ikkense* was isolated from a culture of 50 ml. The cells were harvested by centrifugation and the chromosomal DNA was isolated using conventional phenol-chloroform extraction methods (Maniatis et al., 1982). The DNA was partially digested using Sau3AI (New England Biolabs, MA, USA), and fragments with the lengths between 3 kb and 10 kb were purified from an agarose gel using the QIAquick Gel Extraction Kit (Qiagen, Hilden, Germany) as described by the producer.

The vector for cloning chromosomal DNA from *A. ikkense* was a modified pUC18 plasmid (Stratagene, CA, USA). Plasmid pUC18 was restricted by NdeI and HindIII endonucleases (New England Biolabs). The sticky ends were refilled using Klenow fragment of DNA polymerase (New England Biolabs) and the blunt ends were ligated using T4 DNA ligase (New England Biolabs). DNA sequencing of the modified pUC18 plasmids, denoted pUC18dlacZ, at GATC Biotech AG (Konstanz, Germany) and analysis of the DNA sequence in the CLC Workbench 4 software (CLC bio, Aarhus, Denmark) confirmed that the α-subunit sequence of pUC18 was deleted in plasmid pUC18dlacZ. Thus, plasmid pUC18dlacZ was not able to mediate α-complementation when introduced into *E. coli* cells harbouring the beta-galactosidase ΔZ15 mutation.

Sau3AI restricted and gel-purified chromosomal DNA from *A. ikkense* was ligated into plasmid pUC18dlacZ treated with the restriction endonuclease BamHI and Antarctic Phosphatase (New England Biolabs). The ligation mixture was transformed into chemically competent *E. coli* TOP10 cells. Transformed cells were plated onto LB agar (10 g/l Bacto tryptone, 5 g/l yeast extract, 10 g/l NaCl) containing 20 µg/ml X-gal, 0.1 mM IPTG, and 100 µg/ml ampicillin and incubated over night at 37° C. After a 16 hours over night incubation, the plates were transferred to 20° C. and incubated for another 20 hours. A total of 580 colonies were screened and 1 blue colony was detected. The colony that turned blue during incubation at 20° C. was selected and transferred to 10 ml LB broth and grown at 37° C. over night. Recombinant *E. coli* cells from over night cultures were harvested by centrifugation, and plasmid DNA was purified using the QIAprep Spin Miniprep Kit (Qiagen). Plasmid DNA was analysed for inserts by digestion with restriction endonucleases EcoRI and PstI (New England Biolabs). The insert in the plasmid, denoted pUCIkka-bgal, was sequenced at GATC Biotech AG (Konstanz, Germany) using primer walking with the primer M13 reverse and custom made primers specific for the insert in pUCIkka-bgal (SEQ ID 3: 5'CCGTCATCCATATCACC3'; SEQ ID 4: 5'CCTTTGCCCAAGAGCCAACC3'; SEQ ID 5: 5'GCTATTATCAGACTTGGCACC3'; SEQ ID 6: 5'GTAAT-TCAAT GTTCCAACGTG3'; Seq ID 7: 5'CGCTTATGGT-GTGAAG3') and a sequence just downstream of the multiple cloning site in pUC18dlacZ, (SEQ ID 8: 5'GGGCTGGCT-TAACTATGCGG3'). The Ikka-beta-galactosidase gene sequence harboured by the DNA insert is shown as SEQ ID NO 2.

4.2 Characterization of the Ikka-Beta-Galactosidase Gene Sequence

Analysis of the DNA sequence, SEQ ID NO 2, using the CLC Workbench 4 software (CLC bio, Aarhus, Denmark) showed an open reading frame with the coding capacity of 1,041 amino acids, SEQ ID NO 1. The NCBI search tool Blastp was used to search for related sequences in databases. The closest related sequences were beta-galactosidases from *Bacillus megaterium* (accession no ABN13675) 56.7% identity, *Paenibacillus* sp. JDR-2 (accession no ZP_02849115) 55.3% identity, and *Geobacillus* sp. Y412MC10 (accession no ZP_03036811) 54% identity, all of which belong to the Glycosyl Hydrolase Family 2. Thus, it is concluded that the Ikka-beta-galactosidase belongs to this family. The calculated subunit molecular weight and pI of the Ikka-beta-galactosidase was 119 kDa and pI 5.0, respectively (ExPASy ProtParam tool). The calculated subunit molecular weight was confirmed by SDS-PAGE, FIGS. 5 and 6. Alignment of the Ikka-beta-galactosidase with structurally resolved enzymes showed that the conserved active site region in *E. coli* (ILCEYAHAMGN) (pos. 534-544) (Gebler et al. 1992) is well conserved in the Ikka-beta-galactosidase (ILCEFSHAMGN) (pos. 547-557), and the active site nucleophile Glu-537 is probably found as Glu-550.

Example 5

Production of Recombinant Ikka-Beta-Galactosidase in *Escherichia coli*

Native *Alkalilactibacillus ikkense* was shown to produce only moderate amounts of Ikka-beta-galactosidase. Therefore, in order to produce larger amounts of the beta-galactosidase, subcloning of the Ikka-beta-galactosidase gene into expression plasmids was carried out.

5.1 Construction of a Vector for the Expression of Recombinant Ikka-Beta-Galactosidase in *Escherichia coli*.

The Ikka-beta-galactosidase gene was subcloned further using chromosomal DNA from *A. ikkense* as template and the PCR primers bGa15': 5'CTGAATTCGCATATGGCAAAAAAATTAAAAAAATTC3' (EcoRI restriction site underlined) (SEQ ID 9), and bGa13': 5'CCAAGCTTATCTGTTTAAACTATTCAACATG3' (HindIII site double underlined) (SEQ ID 10). The polymerase used was the proofreading polymerase Phusion® High-Fidelity DNA Polymerase (New England BioLabs). The PCR reaction was analyzed by gel electrophoresis on a 0.8% agarose gel (Seakem GTG) and the 3.9 kb fragment was ligated into pJET1.2/blunt cloning vector (Fermentas, Helsingborg, Sweden) and transformed into *E. coli* TOP10 cells. *E. coli* transformants containing pJET1.2/blunt were isolated on ampicillin containing LB agar plates and plasmid DNA was prepared as described above. Plasmid DNA was restricted with the enzymes EcoRI and HindIII and analysed on 0.8% (w/v) agarose gels as described. The 3.9 kb DNA fragment was purified from the gel using the QIAquick Gel Extraction Kit as described by the producer. The purified DNA fragment was ligated into plasmid pUC18dlacZ similar restricted with the enzymes EcoRI and HindIII and gel purified as described above. The ligation mixture was transformed into *E. coli* TOP10 cells and recombinant cells harbouring the plasmid pUC18dlacZ with the Ikka-beta-galactosidase gene were selected as blue colonies on LA plates containing 100 μg/ml ampicillin, 1 mM IPTG, and 40 μg/ml X-gal. Transformants were selected and analysed for plasmids and inserts. Plasmid DNA was prepared from a 10 ml culture and the DNA was sent for sequencing at GATC biotech (Konstanz, Germany) using the primers described above in 4.1. The entire Ikka-beta-galactosidase gene was sequenced on both strands in order to ensure that no mutations were introduced during PCR. One of the recombinant clones, which contained plasmid pUC18dlacZ with the Ikka-beta-galactosidase gene, denoted plasmid pUCIkka-bgal_exp, was selected for further expression studies.

5.2 Expression of Recombinant Ikka-Beta-Galactosidase in *Escherichia Coli*.

*E. coli* TOP10 cells harbouring plasmid pUCIkka-bgal and pUCIkka-bgal_exp were cultivated in 30 ml LB broth containing 100 μg/ml ampicillin over night at 37° C. After an over night incubation, the cells were supplemented with 0.1 mM IPTG and incubated at 20° C. for further 20 hours. Cells were harvested by centrifugation for 30 min at 4,700 rpm at 10° C.

and resuspended in 1 ml 0.1 M $NaH_2PO_4/Na_2HPO_4$, pH 7. The cells were lysed by bead beating in a Fast Prep instrument (Fast Prep FP120, Bio101/Savant Instruments Inc., Holbrook, N.Y.) at speed 5.5 for 3 times 25 sek. The samples were cooled on ice in between the beating/shaking. The lysate was centrifuged at 10,000 g for 15 min at 4° C., and the supernatant containing the Ikka-beta-galactosidase enzyme was transferred to a clean tube. This crude extract was used for subsequent analyses.

5.3 Properties of Recombinant Ikka-Beta-Galactosidase Produced in *Escherichia coli*.

5.3.1. SDS-PAGE of Recombinant Ikka-Beta-Galactosidase and Determination of Yield Produced.

Intracellular extracts from recombinant *E. coli* cells harbouring plasmid pUCIkka-bgal were analysed on SDS-PAGE (SDS gel 4-12%, PAGEgel, CA, USA) as described above in 3.4. Cultures induced with 1 mM IPTG and control cultures not induced were analysed.

Figure 6:
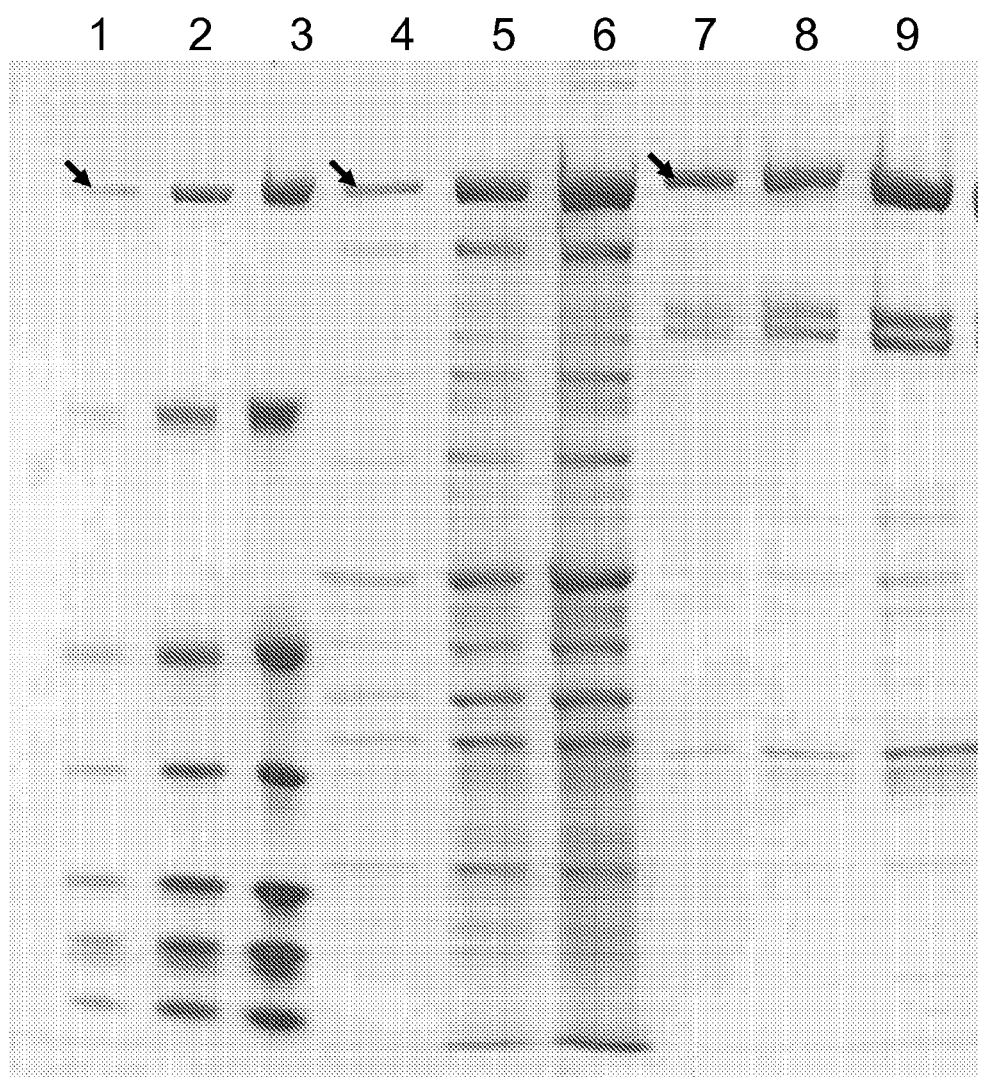
FIG. 6 shows SDS-PAGE of three extract dilutions from recombinant *E. coli* cells expressing Ikka-beta-galactosidase (lanes 4, 5, and 6). For comparison, enzyme extract dilutions with beta-galactosidase from *Kluyveromyces lactis* (lanes 7, 8, and 9) and a molecular weight marker with native *E. coli* beta-galactosidase (marker at 120 kDa) were co-electrophoresed with the recombinant Ikka-beta-galactosidase. Arrows show the position of the 120 kDa beta-galactosidase bands FIG. 7 discloses temperature dependence of recombinant Ikka-beta-galactosidase produced in *E. coli*. Y-axis is the relative activity in percent of the maximal activity. X-axis is the incubation temperature. ♦, indicate recombinant Ikka-beta-galactosidase; ○, indicate *Kluyveromyces lactis* beta-galactosidase.

The protein bands in extracts from cultures grown with and without IPTG were identical apart from a band of approximately 120 kDa in cultures induced with IPTG (arrow in FIG. 6). Thus, as the calculated molecular mass of the Ikka-beta-galactosidase is 119 kDa, and since the strong band at 120 kDa was observed only in cultures induced with IPTG, it is assumed that the 120 kDa band represent the Ikka-beta-galactosidase.

Extracts from cultures of plasmid pUCIkka-bgal harbouring *E. coli* were prepared as described above and diluted before electrophoresis on SDS-PAGE. Beta-galactosidases from *E. coli* (Sigma-Aldrich, MO, USA) and *K. lactis* (Novozymes, Bagsvaerd, Denmark) with known molecular mass and in defined concentrations were co-electrophorezed on the same gel for comparison (arrows in FIG. 6). By comparing the migration and Coomassie Brilliant Blue staining of the known beta-galactosidases with that of the Ikka-beta-galactosidase an estimate of the amount of the Ikka-beta-galactosidase was obtained. The extract, which was used for the subsequent analyses was estimated to have a concentration of Ikka-beta-galactosidase of 2 mg/ml.

5.3.2 Temperature Dependence of Recombinant Ikka-Beta-Galactosidase.

Figure 7:
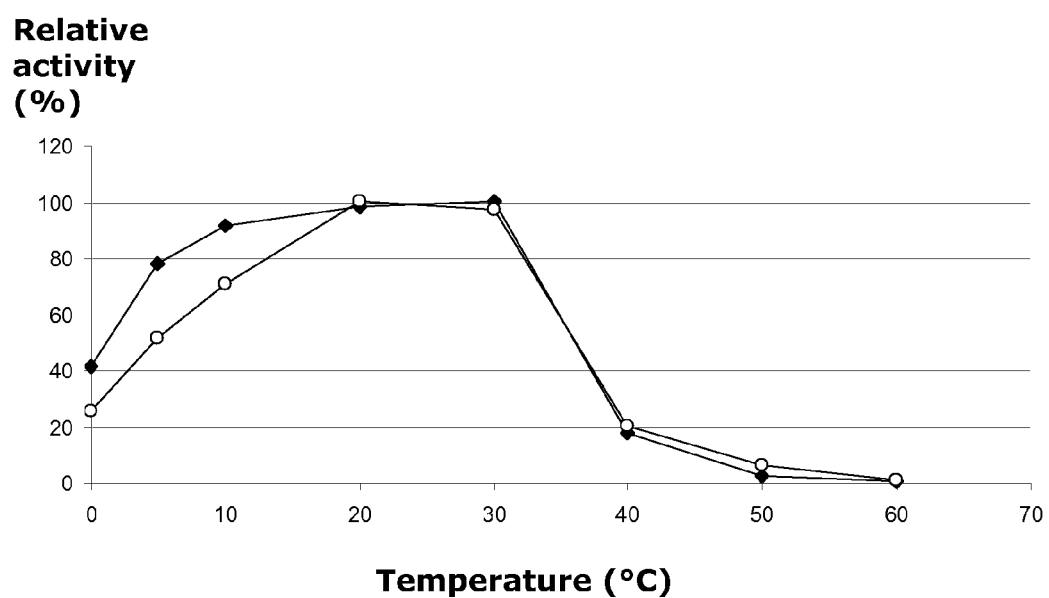
Figure 8:
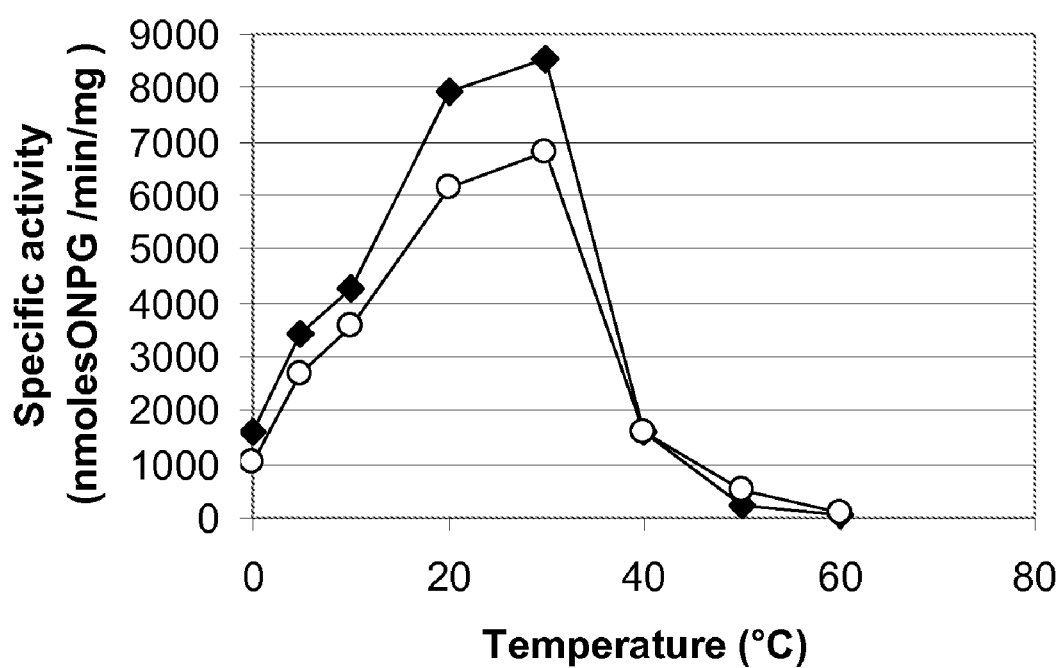
FIG. 8 shows specific activity of recombinant Ikka-beta-galactosidase produced in *E. coli*. Y-axis is specific activity in nmoles ONP released/hour/mg enzyme. X-axis is temperature in ° C. ♦ is recombinant Ikka-beta-galactosidase, ○ is *Kluyveromyces lactis* beta-galactosidase.

The temperature optimum of recombinant Ikka-beta-galactosidase was determined as described above for the native enzyme using ONPG as a substrate. The temperature profile was determined at 0, 5, 10, 20, 30, 40, 50, and 60° C. for 30, 60 and 120 minutes for the recombinant Ikka-beta-galactosidase and, as controls, for the beta-galactosidases from *E. coli* and *K. lactis*. The optimal temperature for activity of the recombinant Ikka-beta-galactosidase was determined to be 20-30° C. (FIG. 7). However, the Ikka-beta-galactosidase also showed high activity at low temperatures with more than 40% activity at 0° C., approximately 80% activity at 5° C. and more than 90% at 10° C. Compared to the *K. lactis* beta-galactosidase, the specific activity of the Ikka-beta-galactosidase was almost twice as high at temperatures between 0° C. and 30° C. (FIG. 8). Both enzymes showed close to zero activity at 40° C. and above (FIG. 8).

Figure 9:
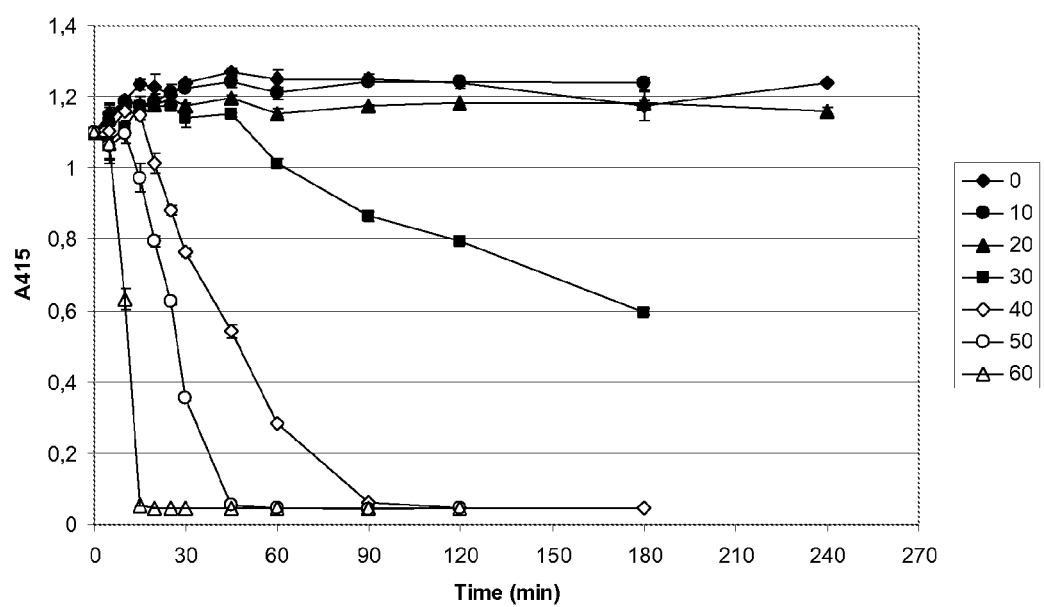
FIG. 9 discloses thermal stability of recombinant Ikka-beta-galactosidase enzyme. An equal amount of enzyme was incubated at the temperature indicated and samples were withdrawn at different time intervals. Y-axis is absorbancy at wavelength 415 nm. X-axis is time in minutes.
Figure 10:
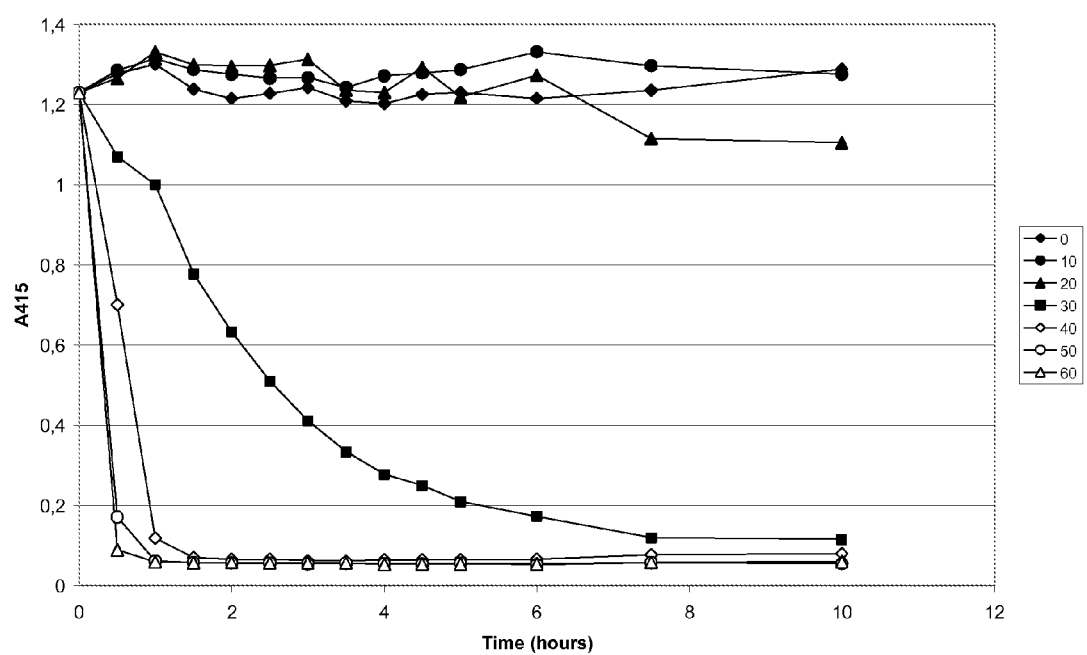
FIG. 10 also discloses thermal stability of recombinant Ikka-beta-galactosidase enzyme, while the X-axis is time in hours.
Figure 11:
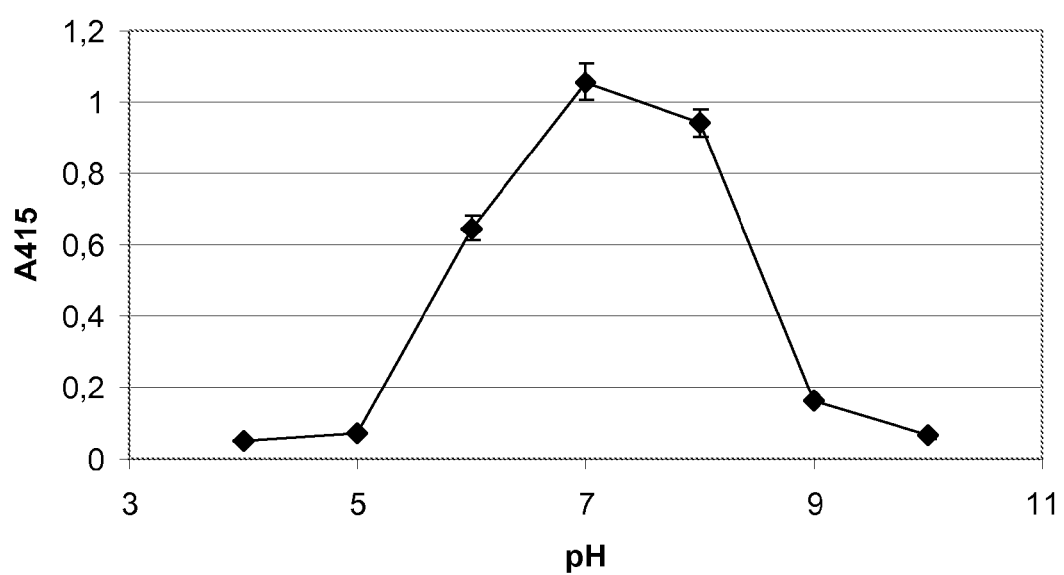
FIG. 11 shows pH dependence of recombinant Ikka-beta-galactosidase. Y-axis is absorbancy measured at wavelength 415. X-axis is pH in the beta-galactosidase assay.

The thermostability of the Ikka-beta-galactosidase was determined at 0, 10, 20, 30, 40, 50, and 60° C. Samples were taken from t=0 hours to t=123 hours with increasing intervals from 5 minutes during the first hour to several hours at the end of the experiment (FIG. 9). FIGS. 9 and 10 show that the Ikka-beta-galactosidase showed high stability at 0° C. and 5° C., at 10° C. the enzyme was stable for approximately 100 hours and at temperatures above 20° C. the Ikka-beta-galactosidase was rather unstable. Treatment at 40° C. for 40 minutes resulted in complete inactivation. The inactivation of the Ikka-enzyme was irreversible.

5.3.3 pH Dependence of Recombinant Ikka-Beta-Galactosidase.

The pH activity profile was studied using a mixed pH buffer (250 mM Tris, 250 mM MES, 250 mM acetic acid) adjusted from pH 4 to pH 10 with HCl or NaOH. The samples were incubated at 20° C. for 2 hours. The optimal pH value for the Ikka-beta-galactosidase was shown to be approximately pH 7.0. At pH 6.0 the enzyme showed 60% of maximal activity and at pH 8.0 the Ikka-enzyme displayed 90% activity. At pH 9.0 15% activity was observed whereas no activity could be detected at pH 5.0 or below or at pH 10 and above.

5.3.3 pH Dependence of Recombinant Ikka-Beta-Galactosidase.

The substrate specificity of the Ikka-beta-galactosidase was determined in assays performed at pH 7.0 and 20° C. for 20 minutes using nine different chromogenic substrates, o-nitrophenyl-beta-D-galactopyranoside, p-nitrophenyl-alpha-D-galactopyranoside, o-nitrophenyl-beta-D-glucopyranoside, p-nitrophenyl-beta-D-glucopyranoside, p-nitrophenyl-beta-D-arabinopyranoside, p-nitrophenyl-beta-D-cellobioside, p-nitrophenyl-beta-D-fucopyranoside, p-nitrophenyl-beta-D-lactopyranoside, and p-nitrophenyl-beta-D-mannopyranoside. Each substrate was used at a concentration of 10 mM. The assays showed that the Ikka-beta-galactosidase was only able to hydrolyze o-nitrophenyl-beta-D-galactopyranoside (ONPG) and p-nitrophenyl-beta-D-fucopyranoside (4% of the relative activity compared to hydrolysis of ONPG). The utilization of the remaining substrates was below detection.

Hydrolysis of lactose was determined in a solution of lactose in water. Three different lactose concentrations were tested: 1.25 mg/ml, 2.5 mg/ml, and 5 mg/ml. Total reaction volume was 0.2 ml and each reaction contained 0.2 mg/ml of recombinant Ikka-beta-galactosidase enzyme. The enzyme reactions were incubated at 5° C. and 20° C., and samples were collected after 15 minutes, 2½ hour, and 24 hours. After incubation, the reactions were stopped by heating at 95° C. for 20 minutes. Visualization of the products was carried out by thin-layer chromatography (TLC) on a TLC Silica gel 60 (Merck, Darmstadt, Germany) in a solvent containing 1-butanol, 2-propanol, and water (3:12:4). Volumes containing 0.005 mg lactose were run on the TLC. Controls were 0.5 µl lactose (2.5%), 0.5 µl galactose (2.5%) and 0.5 µl glucose (2.5%). After being dried, the sugars were visualized by spraying with an orcinol reagent followed by incubation for 5-10 min at 100° C.

Figure 12:
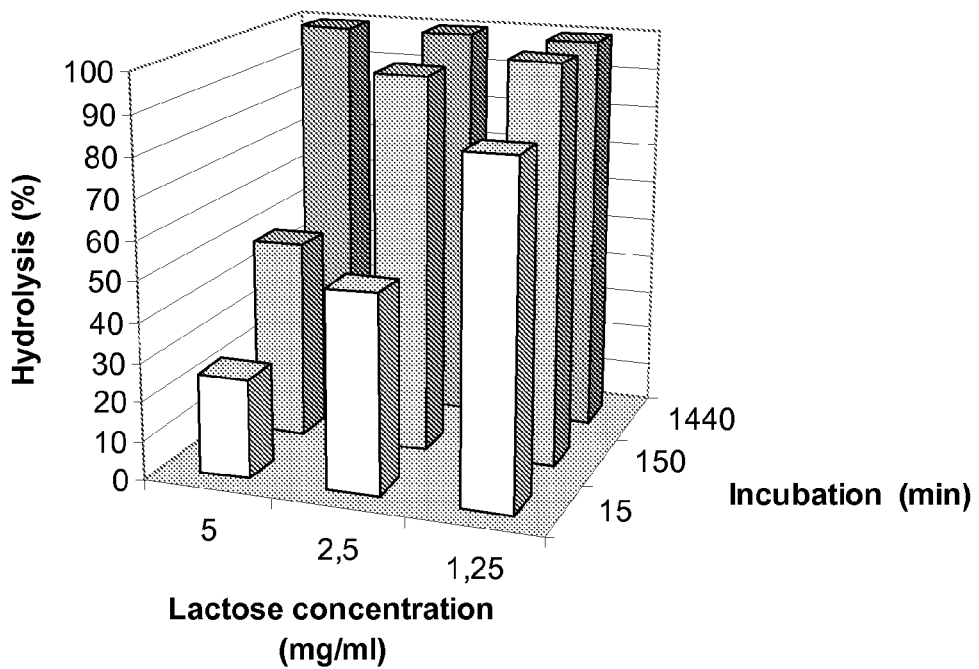
FIG. 12 shows hydrolysis of lactose by recombinant Ikka-beta-galactosidase produced in *E. coli*. The reaction mixture contained lactose in three concentrations, 1.25 mg/ml, 2.5 mg/ml and 5 mg/ml. Samples were withdrawn after incubation for 15, 150, and 1440 minutes. The reactions were incubated at 5° C. (A) or 20° C. (B) and analysed by thin layer chromatography (TLC). The TCL plates were sprayed with an orcinol reagent, and hydrolysis of lactose was estimated by the disappearance of the lactose spots on TLC plates and the concomitant appearance of glucose and galactose spots.
Figure 12:
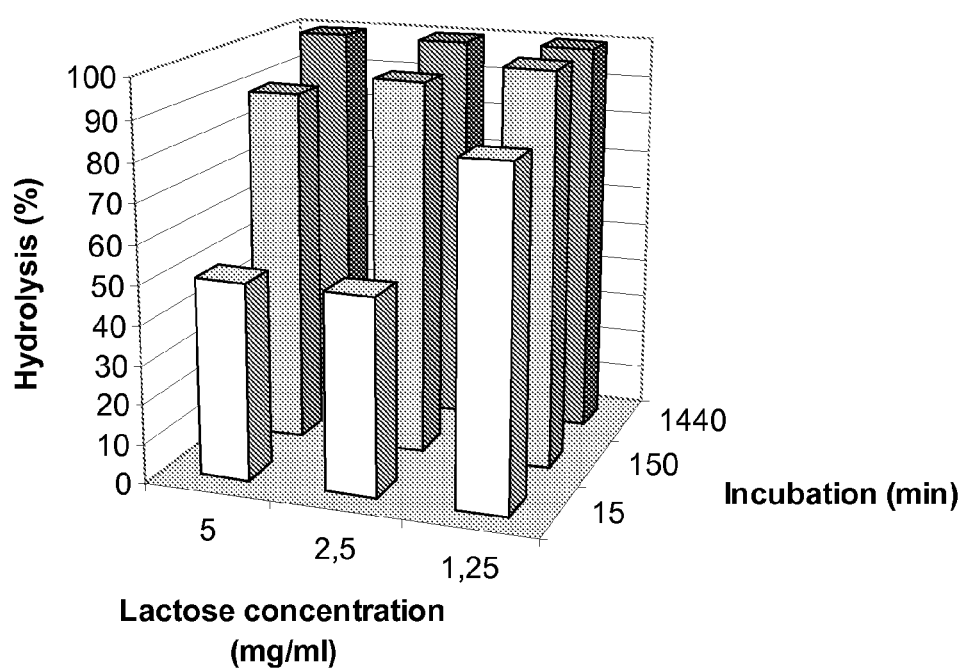

Hydrolysis of lactose was observed both at 5° C. and at 20° C. At 5° C., approximately 75-85% lactose was hydrolysed in the 1.25 mg/ml reaction after 15 minutes and 100% was hydrolysed within 2½ hours, (FIG. 12 A). Similar hydrolysis efficiency was observed in the 1.25 mg/ml reaction incubated at 20° C. (FIG. 12 B). Hydrolysis effectiveness in the 2.5 mg/ml lactose reaction showed approximately 90-95% hydrolysis within 2½ hours at both temperatures. After 24 hours, 100% hydrolysis was observed for all three lactose concentrations at both temperatures (FIG. 12).

5.3.4 Purification of Recombinant Ikka-Beta-Galactosidase.

Beta-galactosidase was purified from crude extracts by ion exchange chromatography. Portions of two ml were subjected to chromatography on a 1 ml High Q cartridge on a BioLogic LP System (Bio-Rad).

The column was washed with 10 ml of 50 mM phosphate buffer (pH 7) and eluted by a gradient from 0 to 1 M of NaCl in 50 mM phosphate buffer (pH 7) at a flow rate of 0.5 ml/min. Fractions of 1 ml were collected. Crude extracts were also subjected to affinity chromatography on a 2 ml column of agarose coupled with p-aminobenzyl-1-thio-beta-D-galactopyranoside (PABTG-agarose, Sigma). The column was washed with 10 ml of 50 mM phosphate buffer (pH 7) before it was eluted by 100 mM NaCl in 50 mM phosphate buffer (pH 7) at a flow rate of 0.5 ml/min. Fractions of 1 ml were collected.

The fractions were analysed for the presence of proteins using a BCA Protein Assay Kit (Pierce), and beta-galactosidase was measured in o-nitrophenyl (ONP)-beta-D-galactopyranoside assays as described above. Fractions containing beta-galactosidase activity were analysed by SDS polyacrylamide gel electrophoresis (4-20%, PAGEgel, CA, USA). Purified beta-galactosidase was used for subsequent stability and activity experiments.

Figure 13:
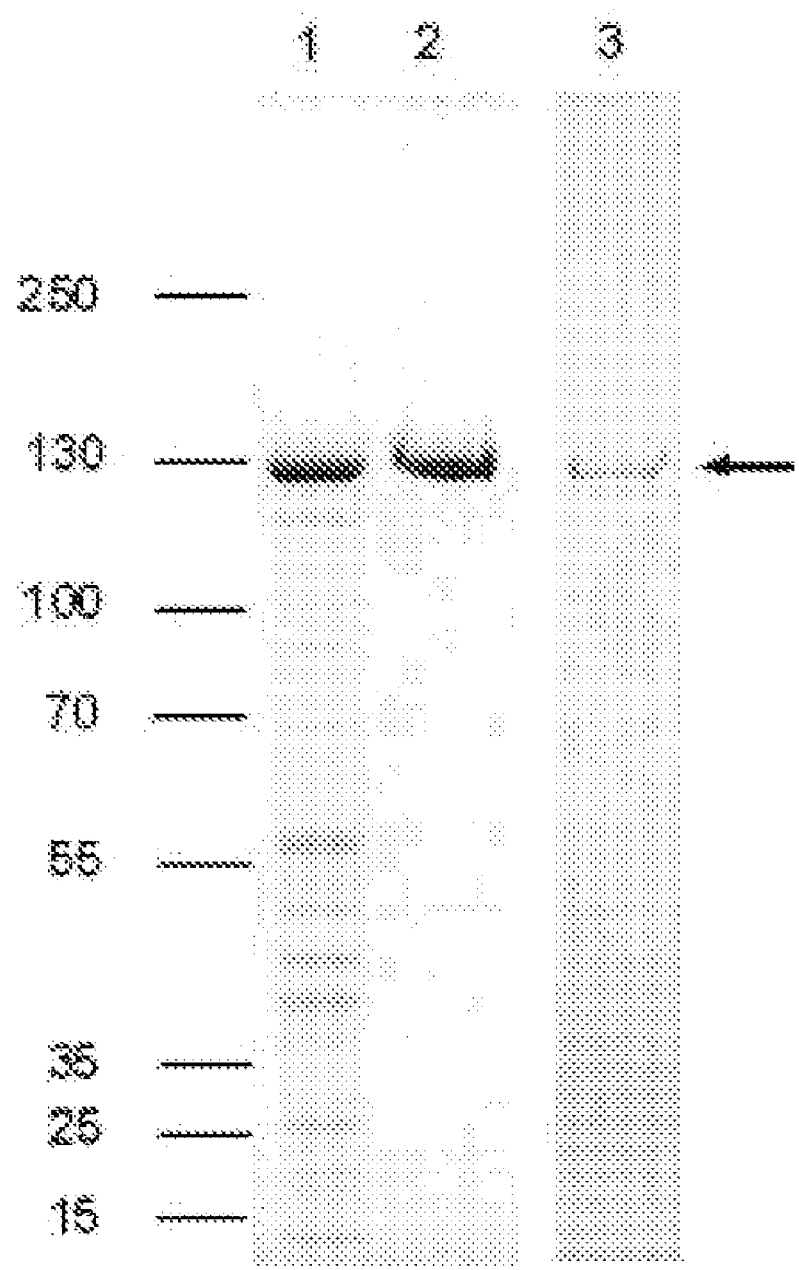
FIG. 13 shows SDS polyacrylamide gel electrophoresis of crude extract of *E. coli* cells expressing *A. ikkense* beta-galactosidase, Lane 1. The beta-galactosidase in the crude extract was further purified on ion exchange chromatography, Lane 2, or on affinity chromatography, Lane 3. The arrow indicates the position of the *E. coli* 120 kDa beta-galactosidase band. Numbers to the left indicate the position of protein bands in the PageRuler™ Plus Prestained Protein Ladder (Fermentas).

FIG. 13 shows that the crude extract from *E. coli* contained recombinant beta-galactosidase with a monomeric molecular weight of approximately 115-120 kDa. Ion exchange chromatography resulted in pure beta-galactosidase (FIG. 13, lane 2), whereas affinity chromatography (FIG. 13, lane 3) only resulted in partially purified recombinant enzyme. Thus, for the subsequent analyses, pure beta-galactosidase from ion exchange was used, unless otherwise specified.

5.3.5 Characterization of Native and Recombinant *A. Ikkense* Beta-Galactosidase.

The molecular weight of the *A. ikkense* beta-galactosidase was determined to be approximately 115-120 kDa when analyzed on SDS-PAGE using known beta-galactosidases from *E. coli* and *K. lactis* as references. This result is in agreement with the calculated molecular weight as determined from the DNA sequence (119 kDa). The crude extract from *E. coli* was estimated to contain 10 mg/ml *A. ikkense* beta-galactosidase.

The specific activity, calculated on the basis of purified beta-galactosidase from ion exchange chromatography was 8.4 micromoles/min/mg protein at 20° C. with ONPG as substrate (Table 1).

TABLE 1

| Purification | Volume (ml) | Protein (mg) | Specific activity (U mg$^{-1}$) | Total activity (U) | Purification (fold) | Recovery (%) |
|---|---|---|---|---|---|---|
| Cell extract | 10 | 30 | 1.6 | 48.0 | 1 | 100 |
| Ion exchange | 10 | 2.5 | 8.4 | 21.1 | 12 | 44 |

A culture of 200 ml *E. coli* cells expressing recombinant *A. ikkense* beta-galactosidase was harvested resulting in a 280 mg wet weight cell pellet. The cells were lyzed in a Fast Prep apparatus, and the extract was subjected to ion exchange chromatography. One U is 1 micromole per min at 20° C. with ONPG as substrate.b Extract of *E. coli* expressing recombinant *A. ikkense* beta-galactosidase was analyzed for beta-galactosidase activity.

Figure 15:
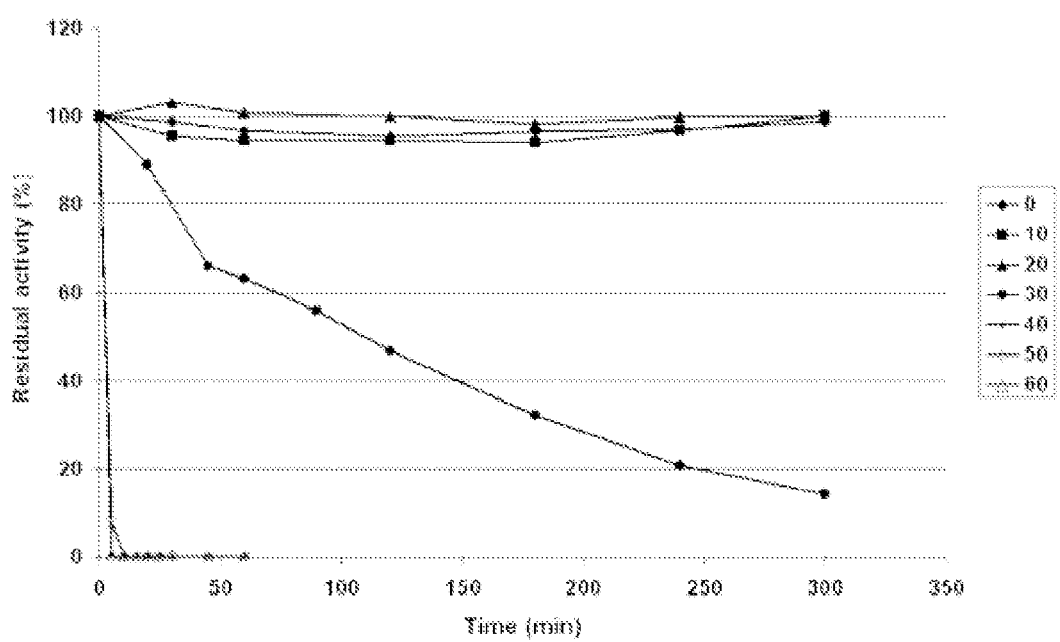
FIG. 15 shows thermal stability of the purified, recombinant *A. ikkense* beta-galactosidase enzyme. An equal amount of enzyme was incubated at the temperatures indicated and samples were withdrawn at different time intervals. Y-axis is the residual activity in percent of maximal activity. Enzyme samples were incubated at temperatures from 0° C. to 60° C. and at the time points indicated (X-axis), samples were withdrawn and assayed for active beta-galactosidase at 20° C. Assays were performed in triplicates, and standard error was below 0.05.

The thermal stability of the purified, recombinant *A. ikkense* beta-galactosidase enzyme was tested as shown in FIG. 15. An equal amount of enzyme was incubated at the temperatures indicated and samples were withdrawn at different time intervals. Y-axis is the residual activity in percent of maximal activity. Enzyme samples were incubated at temperatures from 0° C. to 60° C. and at the time points indicated (X-axis), samples were withdrawn and assayed for active beta-galactosidase at 20° C. Assays were performed in triplicates, and standard error was below 0.05.

At 0° C. the enzyme displayed more than 60% of the maximal activity, and at 10° C., more than 70% of the maximal activity was observed both for purified recombinant enzyme. Analysis of enzyme stability showed that purified, recombinant beta-galactosidase was 100% stable at 0° C. to 20° C. for at least 5 hours (FIG. 15), and that the residual activity after 5 days storage at 0° C. to 20° C. was 50-60% (data not shown). At 30° C., the purified beta-galactosidase lost more than 80% of its activity within 5 hours. Complete, irreversible inactivation was achieved within 5 minutes at 50° C. and within 10 minutes at 40° C. (FIG. 15).

Figure 14:
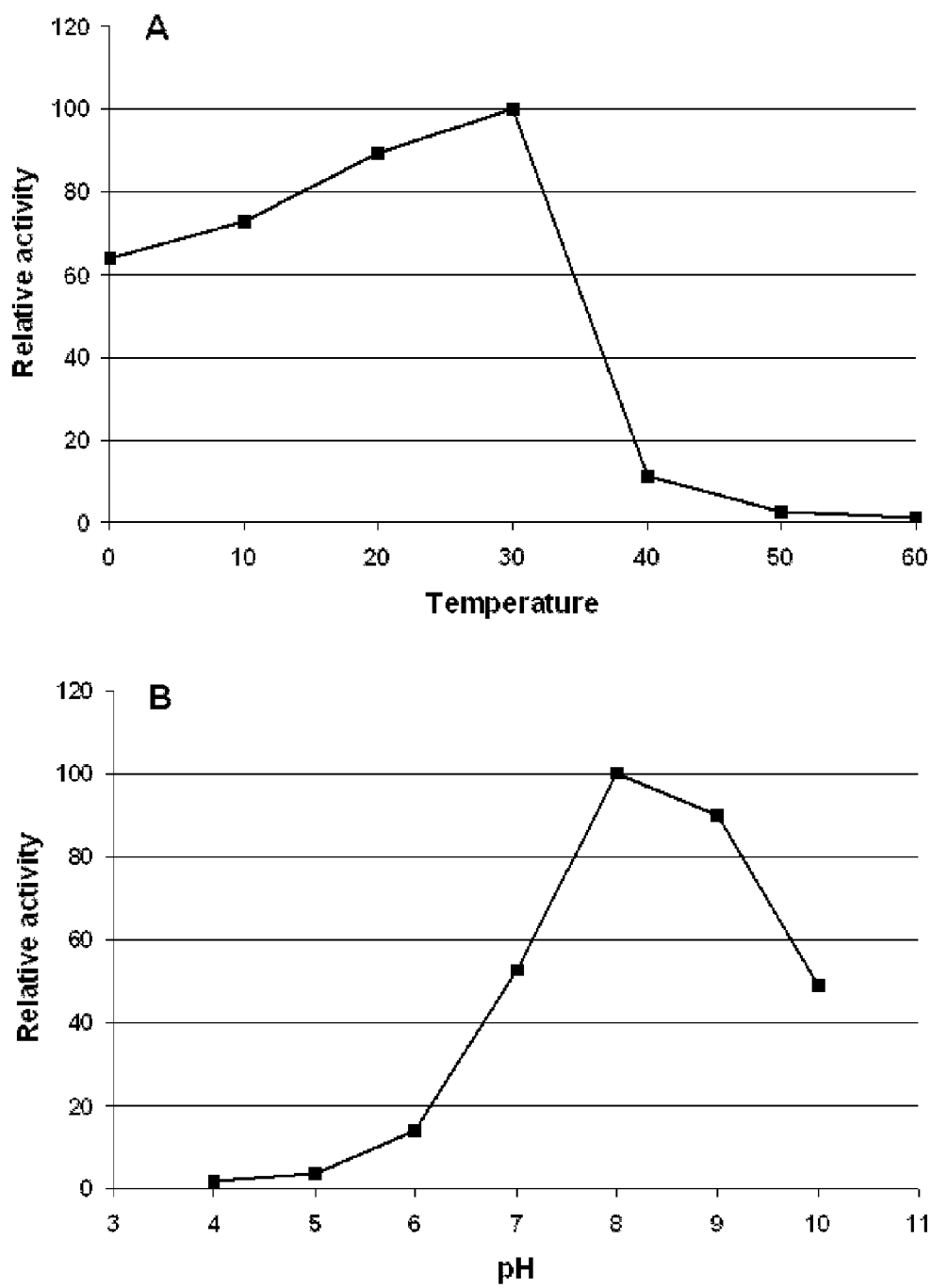
FIG. 14 shows temperature dependence (A) and pH dependence (B) of the purified, recombinant *A. ikkense* beta-galactosidase and of a crude extract containing recombinant enzyme. Y-axis is the relative activity in percent of maximal activity. X-axis is the incubation temperature (A) or pH (B). The relative activity of the purified, recombinant enzyme with ONPG as substrate is illustrated by black squares. Assays were performed in triplicates, and standard error was below 0.05.

The Temperature dependence (A) and pH dependence (B) of the purified, recombinant *A. ikkense* beta-galactosidase was tested (FIG. 14). Y-axis is the relative activity in percent of maximal activity. X-axis is the incubation temperature (A) or pH (B). The relative activity of the purified, recombinant enzyme with ONPG as substrate is illustrated by black squares. Assays were performed in triplicates, and standard error was below 0.05.

Maximal activity of the purified, recombinant enzyme was observed at pH 8 (FIG. 14B). About 60% of the maximal activity was maintained at pH 7, and at pH 9 approximately 90% activity was observed (FIG. 14B).

Figure 16:
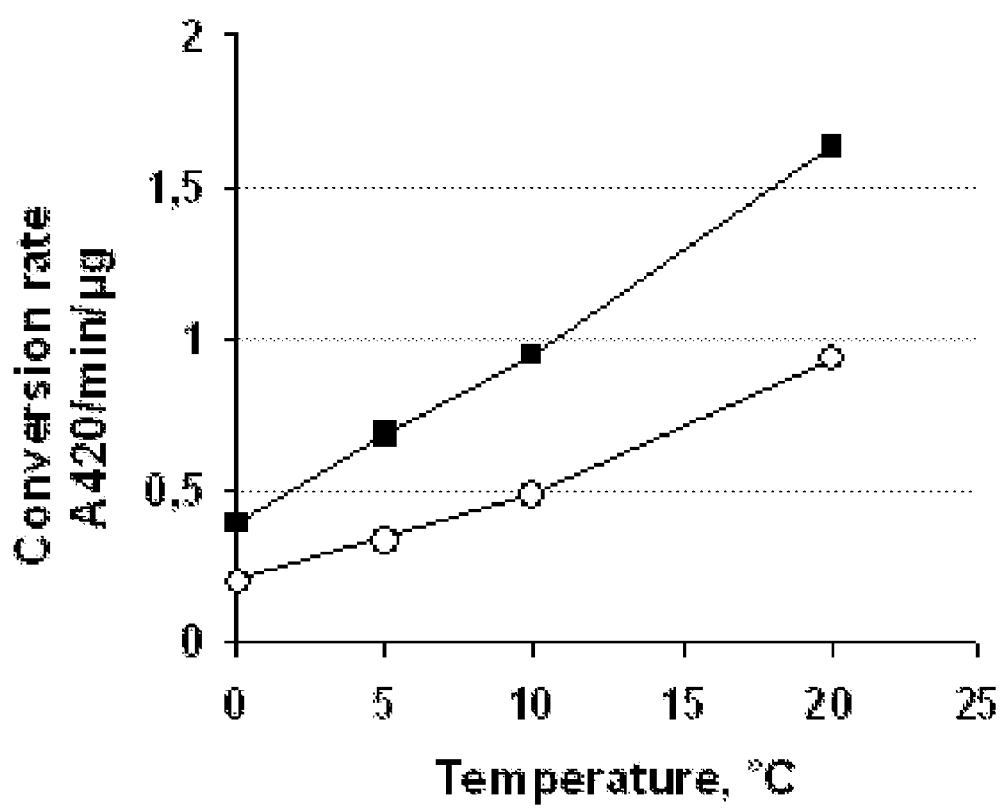
FIG. 16 shows benchmarking the *A. ikkense* beta-galactosidase (black squares) with commercially available Lactozyme® 3 3000 L from *K. lactis* (open circles). An equal amount of enzyme (2 mg/ml) was incubated with ONPG as substrate at temperatures from 0° C. to 20° C. Samples were withdrawn at different time intervals and hydrolyzed ONP was measured at A420 nm. Hydrolysis efficiency was calculated as increase in A420 nm per min per microgram active enzyme. Assays were performed in triplicates, and standard error was below 0.05.

The recombinant *A. ikkense* beta-galactosidase was benchmarked with Lactozyme 3000® 13 from *K. lactis*. At temperatures between 0° C. and 20° C. the *A. ikkense* beta-galactosidase showed a twofold increase in conversion rate, when compared to the *K. lactis*-beta-galactosidase (FIG. 16); *A. ikkense* beta-galactosidase (black squares) compared with commercially available Lactozyme® 3000 L from *K. lactis* (open circles). Specically the experiment was conducted in the following way: An equal amount of enzyme (2 mg/ml) was incubated with ONPG as substrate at temperatures from 0° C. to 20° C. Samples were withdrawn at different time intervals and hydrolyzed ONP was measured at A420 nm. Hydrolysis efficiency was calculated as increase in A420 nm per min per microgram active enzyme. Assays were performed in triplicates, and standard error was below 0.05.

Figure 17:
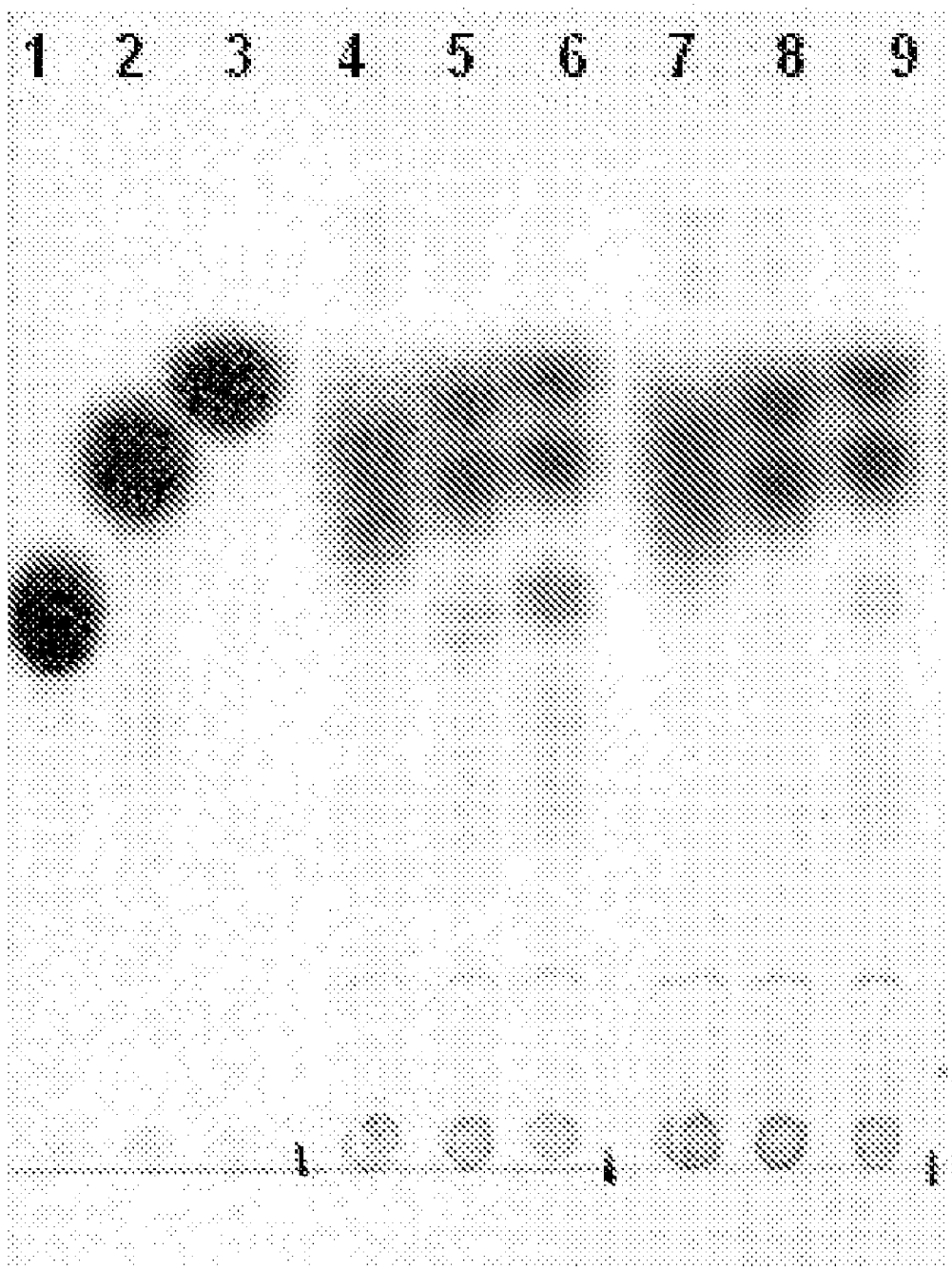
FIG. 17 shows thin-layer chromatography (TLC) of the hydrolysis of lactose by the *A. ikkense* beta-galactosidase. Lanes 4-6: samples incubated at 5° C. for 2½ h (4: 1.25 mg/ml lactose, 5: 2.5 mg/ml lactose, 6: 5 mg/ml lactose). Lanes 7-9: samples incubated at 20° C. for 2½ h (7: 1.25 mg/ml lactose, 8: 2.5 mg/ml lactose, 9: 5 mg/ml lactose). Lanes 1-3: Controls, 0.0125 µg of each of the carbohydrates 13 lactose (lane 1), galactose (lane 2) and glucose (lane 3).

Investigation of substrate specificity of the *A. ikkense* β-galactosidase was carried out using nine different chromogenic substrates. Hydrolysis was only observed with ONPG and with p-nitrophenyl-beta-D-fucopyranoside (4% of the relative activity compared to hydrolysis of ONPG). Thin-layer chromatography (TLC) was used to demonstrate the hydrolysis of lactose by the *A. ikkense* beta-galactosidase (FIG. 17). Lanes 4-6: samples incubated at 5° C. for 2½ h (4: 1.25 mg/ml lactose, 5: 2.5 mg/ml lactose, 6: 5 mg/ml lactose). Lanes 7-9: samples incubated at 20° C. for 2½ h (7: 1.25 mg/ml lactose, 8: 2.5 mg/ml lactose, 9: 5 mg/ml lactose). Lanes 1-3: Controls, 0.0125 mg of each of the carbohydrates lactose (lane 1), galactose (lane 2) and glucose (lane 3).

Hydrolysis of the remaining substrates was below detection limit. Hydrolysis of lactose was observed at both 5° C. and at 20° C. (FIG. 17). At 5° C., approximately 75-85% of the lactose was hydrolyzed in the 1.25 mg/ml reaction after 15 minutes, and 100% of the lactose was hydrolyzed within 2½ hours (FIG. 17, lane 4). Similar hydrolysis efficiency was observed in the 1.25 mg/ml reaction incubated at 20° C. for 2½ hours (FIG. 17, lane 7). Hydrolysis effectiveness in the 2.5 mg/ml lactose reaction showed approximately 90-95% hydrolysis within 2½ hours at both temperatures (FIG. 17, lanes 5 and 8). After 24 hours, 100% hydrolysis was observed for all three lactose concentrations at both temperatures (not shown). At the highest lactose concentration (27 mg/ml), the TLC gel indicated the formation of oligosaccharides (FIG. 17, lanes 6 and 9).

Example 6

Production of Recombinant Ikka-Beta-Galactosidase in *Bacillus Subtilis*

The Ikka-beta-galactosidase was further subcloned in a *Bacillus subtilis* expression vector, pAL10 (MoBiTech, GmbH). PCR was performed using chromosomal DNA from *Alkalilactibacillus ikkense* as template and the PCR primers Bs_pAL_bGa15': 5'GGCCAT GGATCCATGGCAAAAAAATTAAAAAAATTC3' (BamHI restriction site underlined) (SEQ ID NO 11) and Bs_pAL_bGa13': 5'GGCCAT CCCGGGTTATCTGTTTAAACTATTCAACATG3' (XmaI restriction site double underlined) (SEQ ID NO 12). PCR, subsequent isolation of the fragment encoding the Ikka-beta-galactosidase, ligation into pUC18dLacZ and transformation of *E. coli* was as described above in 5.1. Plasmid pUC18dLacZ carrying the Ikka-beta-galactosidase gene was prepared and sequenced, before the plasmid DNA was restricted with restriction endonucleases BamHI and XmaI. The 3.1 kb fragment encoding Ikka-beta-galactosidase was purified, inserted into plasmid pAL10 similarly restricted with BamHI and XmaI, and transformed into *E. coli* as described in 5.1. Recombinant *E. coli* harbouring pAL10 containing the Ikka-beta-galactosidase gene was isolated on LB agar plates containing 100 μg/ml ampicillin. Plasmid pAL10_Ikka-bGal was purified and transformed into *B. subtilis* cells using an electroporation protocol for *B. subtilis* from Eppendorf (Germany) (Protocol No. 4308 915.504-08/2003). Recombinant cells harbouring plasmid pAL10 were selected on LB agar containing 5 μg/ml chloramphenicol.

Production of recombinant Ikka-beta-galactosidase in *B. subtilis* was carried out by growing *B. subtilis* pAL10_Ikka-bGal cells in LB containing 5 μg/ml of chloramphenicol at 37° C. for 16 hours. Induction of Ikka-beta-galactosidase synthesis was carried out by changing the temperature to 20° C. *B. subtilis* pAL10_Ikka-bGal cells were cultivated at 20° C. for another 5 hours after which, the cells were harvested, and intracellular enzyme was isolated by Fast Prep as described in 5.2.

A crude, intracellular extract from *B. subtilis* pAL10_Ikka-bGal cells was analysed in ONPG assays as described in 5.3. ONPG assays showed the presence of a cold-active Ikka-beta-galactosidase with an activity similar to the native enzyme, to the recombinant enzyme in crude *E. coli* extracts, and to the pure enzyme produced in *E. coli* cells.

REFERENCES

Cieslinski, H., Kur, J., Bialkowska, A., Baran, I., Makowski, K., and Turkiewicz, M. (2005) Cloning and expression, and purification of a recombinant cold-adapted β-galactosidase from Antarctic bacterium *Pseudoalteromonas* sp. 22b. Prot. Expres. Purific.

Cashion, P., Hodler-Franklin, M. A., McCully, J. and Franklin, M. (1977) A rapid method for base ratio determination of bacterial DNA, Anal. Biochem. 81: 461-466.

Coker, J. A., Sheridan, P. P., Loveland-Curtze, J., Gutshall, K. R., Auman, A., and Brenchley, J. E. (2003) Biochemical characterization of a β-galactosidase with low temperature optimum obtained from an Arctic *Arthrobacter* isolate. J. Bacteriol. 185: 5473-5482.

Coombs, J. M. and Brenchley, J. E. (1999) Biochemical and phylogenetical analysis of a cold-active β-galactosidase from the lactic acid bacterium *Carnobacterium piscicola* BA. Appl. Environ. Microbiol. 65: 5443-5460.

De Ley, J., Cattoir, H. and Reynaerts, A. (1970) The quantitative measurement of DNA hybridization from renaturation rates, Eur. J. Biochem. 12: 133-142.

Fernandes, S., Geueke, B., Delgado, O., Coleman, J., and Hatti-Kaul, R. (2002) β-galactosidase from a cold-adapted bacterium: purification, characterization and application for lactose hydrolysis. Appl. Microbiol. Biotechnol. 58: 313-321.

Gebler, J. C., Aebersold, R., and Withers, S. G. (1992) Glu-537, not Glu-461, is the nucleophile in the active site of (lac Z) beta-galactosidase from *Escherichia coli*. J. Biol Chem 267: 11126-11130.

Hoyoux, A., Jennes, I., Dubois, P., Genicot, S., Dubail, F., Francois, J. M., Baise, E., Feller, G., and Gerday, C. (2001) Cold-adapted β-galactosidase from the Antarctic psychrophile *Pseudoalteromonas haloplanktis*. Appl. Environ. Microbiol. 67: 1529-1535.

Huss, V. A. R. Festl, H., and Schleifer, K. H. (1983) Studies on the spectrophotometric determination of DNA hybridization from renaturation rates, Syst. Appl. Microbiol. 4: 184-192.

Ishikawa, M., Ishizaki, S., Yamamoto, Y., and Yamasato, K. (2002) *Paraliobacillus ryukyuensis* gen. nov., sp. nov., a new Gram-positive, slightly halophilic, extremely halotolerant, facultative anaerobe isolated from a decomposing marine alga, J. Gen. Appl. Microbiol. 48: 269-279.

Ishikawa, M., Nakajima, K., Itamiya, Y., Furukawa, S., Yamamoto, Y., and Yamasato K. (2005) *Halolactibacillus halophiles* gen. nov., sp. nov. and *Halolactibacillus miurensis* sp. nov., halophilic and alkaliphilic marine lactic acid bacteria constituting a phylogenetic lineage in *Bacillus* rRNA group 1, Int. J. Syst. Evol. Microbiol. 55: 2427-2439.

Jørgensen F, Hansen O C, Stougaard P (2004) Enzymatic conversion of D-galactose to D-tagatose: Heterologous expression and characterisation of a thermostable L-arabinose isomerase from *Thermoanaerobacter mathranii* Appl. Environ. Microbiol. 64: 816-822.

Karasová-Lipovová, P., Strnad, H., Spiwok, V., Malá, S, Králová, B., and Russell, N. (2003) The cloning, purification and characterization of a cold-active β-galactosidase-from the psychrotolerant Antactic bacterium *Arthrobacter* sp. C2-2. Enzyme Microbiol. Technol. 33: 836-844.

Lane, D. J. 16S/23S rRNA sequencing, In: E. Stackebrandt, M. Goodfellow (Eds.), Nucleic acid techniques in bacterial systematics, Wiley, New York, 1991, pp. 115-175.

Maniatis, T., Fritsch, E. F, Sambrook, J. (1982). Molecular cloning: a laboratory manual. Cold Spring Harbor, N.Y.: Cold Spring Harbor Laboratory Mesbah, M., Premachandran, U. and Whitman, W. (1989) Precise measurement of the G+C content of deoxyribonucleic acid by high performance liquid chromatography, Int. J. Syst. Bact. 39: 159-167.

Nakagawa, T., Fujimoto, Y., Ikehata, R., Miyaji, T., and Tomizuka, N. (2006) Purification and molecular characterization of cold-active β-galactosidase from *Arthrobacter* psychrolactophilus strain F2. Appl. Microbiol. Biotechnol. 72: 720-725.

Nakagawa, T., Fujimoto, Y., Uchino, M., Miyaji, T., Takano, K. and Tomizuka, N. (2006) Isolation and characterization of psychrophiles producing cold-active β-galactosidase. Lett. Appl. Microbiol. 37: 154-157.

Nakagawa, T., Ikehata, R., Uchino, M., Mijaji, T., Takano, K., and Tomizuka, N. (2006) Cold-active acid β-galactosidase activity of isolated psychrophilic basidiomycetous yeast *Guehomyces pulluland*. Microbiol. Res. 161: 75-79.

Nakayama, et al., Bio-Jikken-Illustrated, vol. 2, "Idenshi-Kaiseki-No-Kiso (A Basis for Gene Analysis)", pp. 148-151, Shujunsha, 1995.

Sorokin, I. D., Zadorina, E. V., Kravchenko, I. K., Boulygina, E. S., Tourova, T. P., and Sorokin, D. Y. (2008) *Natronobacillus azotifigens* gen. nov., sp. nov., an anaerobic diazotrophic haloalkalophile from soda-rich habitats. Extremophiles 12: 819-827.

Stoll, V. S, and Blanchard, J. S. (1990) Buffers: Principles and practice. Methods Enzymol. 182: 24-38.

Turkiewicz, M., Kur, J., Bialkowska, A., Cieslinski, H., Kalinowska, H., Bielecki, S. (2003) Antarctic marine bacterium *Pseudoalteromonas* sp. 22b as a source of cold-adapted β-galactosidase. Biomolec. Engineer. 20: 317-324.

Van de Peer, Y. De Wachter, R. (1994) TREECON for Windows: a software package for the construction and drawing of evolutionary trees for the Microsoft Windows environment, Comput. Appl. Biosci. 10 569-570.

Wainø, M., Tindall, B. J., Schumann, P., and Ingvorsen, K. (1999) *Gracilibacillus* gen. nov., with description of *Gracilibacillus halotolerans* gen. nov., sp. nov.; transfer of *Bacillus dipsosauri* to *Gracilibacillus dipsosauri* comb. nov., and *Bacillus salexigens* to the genus *Salibacillus* gen. nov., as *Salibacillus salexigens* comb. nov., Int. J. Syst. Bacteriol. 49: 821-831.

Wayne, L. G., Brenner, D. J., Colwell, R. R., Grimont, P. A. D., Kandler, O., Krichevsky, M. I., Moore, L. H., Moore, W. E. C., Murray, R. G. E., Stackebrandt, E., Starr, M. P. and Trüper, H. G. (1987) Report of the ad hoc committee on reconciliation of approaches to bacterial systematics, Int. J. Syst. Bacteriol. 37: 463-464.

Zhilina, T. N., Garnova, E. S., Tourova, T. P., Kostrikina, N. A. and Zavarzin, G. A. (2001) *Amphibacillus fermentum* sp. nov., *Amphibacillus tropicus* sp. nov., new alkaliphilic, facultatively anaerobic, saccharolytic bacilli from Lake Magadi, Microbiology (English translation of Mikrobiologiia) 70: 711-722.

Zhilina, T. N., Garnova, E. S., Tourova, T. P., Kostrikina, N. A. and Zavarzin, G. A. (2002) *Amphibacillus fermentum* sp. nov. and *Amphibacillus tropicus* sp. nov. In Validation of Publication of New Names and New Combinations Previously Effectively Published Outside the IJSEM, List no. 85, Int. J. Syst. Evol. Microbiol. 52: 685-690.

```
SEQ ID NO: 1
(1) GENERAL INFORMATION:
(i) APPLICANT:
(A) NAME: University of Copenhagen
(B) STREET:
(C) CITY:
(D) COUNTRY:
(E) POSTAL CODE:

(ii) TITLE OF INVENTION: Cold-active beta-galactosidase,
a method of producing same and use of such enzyme (iii) NUMBER OF SEQUENCES: 10

(2) INFORMATION FOR SEQ ID NO: 1
```

-continued (i) SEQUENCE CHARACTERISTICS:
(A) LENGTH: 1,041 amino acids
(B) TYPE: amino acid
(C) STRANDEDNESS: Not relevant
(D) TOPOLOGY: linear (ii) MOLECULE TYPE: protein (xi) SEQUENCE DESCRIPTION SEQ ID NO: 1

```
  1                                       10
Met Ala Lys Lys Leu Lys Lys Phe Asn Tyr Leu Pro Pro Lys Asn
                  20                              30
Gly Tyr Pro Glu Trp Asn Asn Asn Pro Glu Ile Phe Gln Leu Asn
                          40
Arg Arg Glu Ala His Ala Thr Leu Val Pro Tyr Ser Asn Leu Glu
          50                                      60
Leu Ala Leu Lys Gly Glu Arg Thr Ala Ser Ser Phe Tyr Gln Ser
                                  70
Leu Asn Gly Ser Trp Gln Phe Ala Phe Ala Gln Glu Pro Thr Lys
                  80                              90
Arg Val Ile Asp Phe Tyr Arg Lys Asp Phe Asp His Arg Asp Trp
                                 100
Asp Ser Ile Lys Val Pro Ser His Trp Gln Leu Glu Gly Tyr Asp
                 110                             120
Tyr Pro Gln Tyr Thr Asn Thr Thr Tyr Pro Trp Val Glu Lys Glu
                                 130
Thr Ile Lys Pro Pro Phe Ala Pro Thr Asn Tyr Asn Pro Val Gly
                 140                             150
Gln Tyr Val Arg Thr Phe Glu Leu Pro Thr Asp Trp Asn Gly Ala
                                 160
Pro Val Tyr Leu Asn Phe Gln Gly Val Glu Ser Ala Phe Tyr Val
                 170                             180
Trp Ile Asn Gly Asp Leu Val Gly Tyr Ser Glu Asp Thr Phe Thr
                                 190
Pro Ala Glu Phe Asp Ile Thr Pro Tyr Leu Ile Glu Gly Glu Asn
                 200                             210
Lys Leu Ala Val Glu Val Tyr Arg Trp Ser Asp Ala Ser Trp Leu
                                 220
Glu Asp Gln Asp Phe Trp Arg Leu Ser Gly Ile Phe Arg Asp Val
                 230                             240
Tyr Leu Tyr Ala Thr Pro Ala Gln His Ile Asp Asp Phe Val
                                 250
Thr His Glu Leu Asp Ala Asp Tyr Arg Asn Ala Thr Leu Lys Ile
                 260                             270
Asp Met Lys Val Arg Asp Tyr Phe Glu Ile Gly Glu Pro Val Thr
                                 280
Val Asn Ala Met Leu Phe Asp Leu Asn Gly Asn Pro Val Leu Lys
                 290                             300
Gln Pro Leu Leu Ser Ala Val Asp Phe Ser Gly Lys Glu Val Ala
                                 310
Asp Val Ser Val Ile Thr Thr Ile Asp Asn Pro Leu Lys Trp Ser
                 320                             330
Ala Glu Asp Pro Asn Leu Tyr Thr Leu Val Leu Ser Leu Val Asp
                                 340
Gln Asn Gly Lys Leu Leu Glu Thr Glu Ser Cys Arg Val Gly Phe
                 350                             360
Arg Lys Phe Glu Arg Lys Asp Gly Leu Met Gln Ile Asn Gly Lys
```

-continued

```
                       370
Arg Ile Val Phe Lys Gly Thr Asn Arg His Glu Phe Ala Ser Asp
            380                             390
Lys Gly Arg Ala Ile Thr Ile Asp Asp Met Val Asn Asp Ile Gln
                           400
Leu Met Lys Gln His Asn Ile Asn Ala Val Arg Thr Ser His Tyr
            410                             420
Pro Asn His Pro Leu Trp Tyr Glu Leu Cys Asp Thr Tyr Gly Leu
                           430
Tyr Val Ile Asp Glu Thr Asn Leu Glu Thr His Gly Thr Trp Val
            440                             450
Tyr Gly Gln Lys Gly Leu Ala Glu Thr Ile Pro Gly Ser Leu Pro
                           460
Lys Trp Thr Glu Asn Val Leu Asp Arg Cys Asn Ser Met Phe Gln
            470                             480
Arg Asp Lys Asn His Pro Ser Ile Leu Asp Trp Ser Leu Gly Asn
                           490
Glu Ser Phe Gly Gly Asp Asn Phe Leu Lys Met His Asp Phe Phe
            500                             510
Thr Glu Gln Asp Pro Ala Arg Leu Val His Tyr Glu Gly Ile Phe
                           520
His Tyr Arg Glu Ser Glu Arg Ala Ser Asp Met Glu Ser Thr Met
            530                             540
Tyr Ile Ser Pro Glu Gly Ile Glu Asp Tyr Ala Lys Lys Ala Thr
                           550
Lys Glu Thr Lys Pro Tyr Ile Leu Cys Glu Phe Ser His Ala Met
            560                             570
Gly Asn Ser Leu Gly Asn Phe Tyr Lys Tyr Thr Glu Leu Phe Asp
                           580
Gln Tyr Pro Ile Leu Gln Gly Gly Phe Ile Trp Asp Trp Lys Asp
            590                             600
Gln Ser Leu Leu Thr Lys Thr Ala Gly Gly Thr Pro Tyr Leu Ala
                           610
Tyr Gly Gly Asp Phe Gly Glu Ser Pro His Asp Gly Asn Phe Ala
            620                             630
Gly Asn Gly Leu Ile Phe Gly Asp Gly Lys Val Ser Pro Lys Ile
                           640
Phe Glu Val Lys Arg Cys Tyr Gln Asn Val Asp Phe Lys Ala Ile
            650                             660
Asp Leu Val His Gly Gln Ile Glu Leu Thr Asn Lys Tyr Leu Phe
                           670
Thr Asn Leu Ala Asp Tyr Gln Leu Asn Trp Val Ile Thr Arg Asn
            680                             690
Gly Asp Ala Ile Glu Ser Gly Ala Thr Asn Ile Asn Val Leu Pro
                           700
Gly Glu Lys Arg Glu Val Ile Leu Asp Tyr Thr Phe Pro Thr Gly
            710                             720
Val Cys Met Thr Asp Glu Tyr Ile Leu Thr Leu Arg Phe Ser Glu
                           730
Lys Gly Asp Arg Leu Trp Cys Glu Ala Gly His Glu Val Ala Phe
            740                             750
Asn Gln Phe Val Leu Pro Thr Lys Val Thr Lys Leu Arg Glu Lys
                           760
Thr Gln Asp Thr Lys Thr Leu Ser Val Glu Val Met Gln Asp Arg
```

```
                            770                             780
Leu Val Thr Ser Gly Ala Gly Phe Ser Val Gly Phe Asp Thr Lys

790
Ser Gly Met Leu Val Ser Tyr Gln Val Gly Asn Glu Leu Val 800                             810
Lys Glu Ala Leu Val Pro Asn Phe Trp Arg Ala Met Thr Asp Asn

820
Asp Arg Gly Asn Gly Leu Asp Gln Arg Ser Gln Ile Trp Arg Asp 830                              840
Ala Asn Glu Val Arg Glu Leu Val Ser Phe Gln Tyr Glu Val Leu

850
Thr Asn Arg Val Ser Ile Ser Thr Val Phe Leu Tyr Glu Asp Leu 860                              870
Asn His Ser Arg Val Glu Leu Asn Phe Leu Ile Thr Gly Thr Gly

880
Glu Ile Lys Val Asp Tyr Val Leu Lys Pro Gly Glu Asp Leu Pro 890                              900
Glu Ile Pro Glu Ile Gly Leu Met Leu Thr Met Pro Lys Ser Phe

910
Asp Gln Leu Ser Trp Tyr Gly Lys Gly Pro His Glu Ser Tyr Trp 920                              930
Asp Lys Gln Lys Gly Ala Lys Ile Gly Leu Tyr Gln Gly Phe Val

940
Gly Asp Gln Tyr Val Pro Tyr Leu Lys Pro Gln Glu Cys Gly Asn 950                              960
Lys Val Gly Val Arg Ser Ala Glu Leu Val Asn Asp Val Gly Val

970
Gly Leu Ile Ile Ser Gly Leu Pro Thr Leu Glu Leu Asn Val Leu 980                              990
Pro Tyr Thr Pro Val Gln Leu Glu Ser Ala Asp His Ser Tyr Gln

1000
Leu Pro Glu Thr Asp Gln Thr Val Val Arg Ile Asn Leu Gly Gln 1010                                   1020
Met Gly Val Gly Gly Asp Asp Ser Trp Gly Gln Arg Thr His Gln

1030
Asp Phe Thr Leu Phe Ala Asn Lys Thr Tyr His Tyr Ser Phe Met

1040
Leu Asn Ser Leu Asn Arg

SEQ ID NO: 2
(2) INFORMATION FOR SEQ ID NO: 2

(i) SEQUENCE CHARACTERISTICS:
(A) LENGTH: 3,123 nucleotides
(B) TYPE: nucleic acid
(C) STRANDEDNESS: single
(D) TOPOLOGY: linear (ii) MOLECULE TYPE: genomic DNA (xi) SEQUENCE DESCRIPTION SEQ ID NO: 2
ATGGCAAAAA AATTAAAAAA ATTCAACTAC CTCCCACCAA AAAACGGGTA        50

CCCAGAGTGG AATAATAATC CGGAAATTTT TCAACTTAAT CGAAGAGAGG       100

CGCATGCAAC ATTGGTGCCA TATTCTAATT TGGAATTGGC ACTTAAAGGG       150

GAGCGGACAG CATCATCATT TTATCAATCT TTAAATGGTA GTTGGCAGTT       200

TGCCTTTGCC CAAGAGCCAA CCAAGCGAGT GATAGATTTT TATCGGAAAG       250

ATTTTGATCA TCGCGATTGG GATTCGATTA AAGTACCAAG TCATTGGCAG       300
```

```
TTAGAAGGCT ATGACTACCC GCAATACACC AACACAACGT ACCCATGGGT      350

AGAAAAAGAA ACGATTAAAC CTCCATTTGC ACCAACAAAT TATAATCCAG      400

TCGGACAATA TGTTCGCACG TTTGAATTAC CGACTGATTG GAATGGAGCT      450

CCCGTTTATC TGAATTTCCA AGGTGTTGAA TCAGCTTTCT ACGTCTGGAT      500

AAATGGTGAT TTGGTCGGAT ACAGTGAGGA CACTTTCACA CCAGCTGAAT      550

TTGATATAAC TCCCTATTTA ATAGAGGGTG AAAATAAGCT AGCGGTAGAA      600

GTCTATCGTT GGAGTGATGC GAGCTGGCTT GAAGACCAGG ATTTCTGGAG      650

GTTAAGCGGG ATTTTTCGTG ACGTCTATCT ATATGCAACA CCAGCTCAGC      700

ACATTGATGA TTTCTTTGTC ACACACGAAC TTGATGCAGA CTATCGAAAT      750

GCAACGTTGA AGATTGATAT GAAAGTGCGC GATTATTTCG AGATTGGCGA      800

GCCTGTCACA GTTAATGCGA TGCTCTTTGA TCTTAATGGG AATCCGGTTC      850

TCAAGCAACC GCTTTTATCG GCAGTAGATT TTTCAGGTAA AGAAGTTGCT      900

GATGTGAGCG TAATAACAAC AATTGATAAT CCATTGAAAT GGAGTGCGGA      950

AGATCCCAAT CTGTACACTT TGGTTTTAAG TTTAGTTGAT CAGAATGGCA     1000

AGTTGCTTGA AACAGAAAGC TGTCGCGTTG GATTTCGTAA ATTTGAACGC     1050

AAGGACGGAT TGATGCAAAT TAATGGAAAG CGGATTGTCT TTAAAGGGAC     1100

AAATCGTCAC GAATTCGCTT CTGATAAAGG TCGGGCGATA ACGATAGATG     1150

ATATGGTTAA TGATATTCAG CTGATGAAGC AGCATAACAT TAATGCCGTT     1200

CGAACCTCAC ATTATCCGAA TCATCCGCTT GGTATGAGT TGTGTGATAC      1250

GTATGGGTTA TATGTGATTG ACGAGACAAA CTTAGAGACG CACGGGACAT     1300

GGGTTTATGG TCAAAAAGGA TTGGCTGAGA CAATACCAGG TAGTCTACCA     1350

AAGTGGACTG AAAACGTCTT GGATCGTTGT AATTCAATGT TCCAACGTGA     1400

TAAAAACCAC CCATCGATTC TGGATTGGTC ACTTGGTAAT GAATCTTTTG     1450

GTGGCGATAA CTTCTTGAAG ATGCATGACT TCTTTACGGA ACAAGATCCA     1500

GCTCGTCTGG TGCACTATGA GGGGATTTTT CATTATCGTG AATCTGAACG     1550

GGCATCTGAT ATGGAGAGTA CCATGTATAT TTCGCCAGAA GGCATTGAGG     1600

ACTATGCAAA GAAAGCGACC AAGGAGACGA AACCATATAT TTTATGCGAA     1650

TTCAGCCATG CGATGGGCAA CTCGCTAGGA AACTTTTATA AGTATACCGA     1700

GCTATTTGAT CAATATCCGA TCTTACAAGG AGGCTTCATT TGGGATTGGA     1750

AGGATCAATC GCTGCTAACG AAGACAGCAG GAGGCACACC GTATCTTGCT     1800

TATGGTGGTG ATTTTGGTGA ATCGCCACAC GACGGCAACT TGCTGGTAA      1850

TGGTTTGATT TTTGGAGATG GCAAGGTTAG CCCGAAGATT TTTGAAGTGA     1900

AGCGTTGTTA CCAAAATGTT GATTTCAAAG CAATAGACTT AGTGCACGGA     1950

CAAATCGAAT TGACCAATAA ATACTTGTTC ACCAATCTCG CTGACTACCA     2000

ACTAAATTGG GTTATCACTC GAAACGGTGA TGCAATAGAG TCGGGTGCTA     2050

CTAACATCAA TGTCTTACCA GGTGAAAAAA GAGAGGTTAT ACTTGACTAC     2100

ACGTTCCCAA CAGGCGTTTG CATGACGGAT GAATATATTT TGACCCTTCG     2150

TTTTTCTGAG AAAGGTGATC GCTTATGGTG TGAAGCGGGA CATGAAGTTG     2200

CATTTAATCA GTTTGTTTTA CCAACAAAAG TTACGAAATT ACGTGAGAAG     2250

ACACAAGATA CCAAGACGCT TTCAGTTGAA GTAATGCAAG ATCGACTTGT     2300

TACATCTGGT GCTGGATTTA GCGTCGGATT TGACACTAAA TCGGGTATGC     2350
```

-continued

```
TTGTTTCTTA CCAAGTTGGA GGTAATGAAT TGGTGAAAGA GGCACTTGTG    2400

CCAAACTTCT GGCGTGCAAT GACTGATAAT GATCGCGGGA ACGGACTCGA    2450

TCAACGGAGT CAGATTTGGC GTGATGCAAA TGAGGTACGT GAATTGGTTT    2500

CATTTCAGTA TGAAGTGTTG ACCAATAGAG TAAGCATATC AACGGTTTTC    2550

TTATATGAAG ACCTCAACCA TTCACGCGTT GAACTTAACT TTTTGATTAC    2600

TGGAACTGGT GAAATAAAGG TGGATTATGT ACTGAAACCG GGAGAAGATT    2650

TACCAGAAAT ACCAGAGATA GGTTTGATGT TAACGATGCC TAAGTCGTTT    2700

GATCAGTTAA GTTGGTATGG AAAAGGCCCA CATGAATCGT ATTGGGATAA    2750

ACAAAAGGC GCGAAAATAG GTCTTTATCA AGGATTTGTC GGCGATCAGT    2800

ATGTGCCGTA TTTGAAACCA CAAGAATGTG CAACAAAGT AGGAGTTCGT    2850

TCAGCAGAAT TGGTTAATGA TGTTGGTGTT GGTTTGATTA TAAGTGGACT    2900

TCCAACGCTG GAGTTAAATG TCTTACCATA CACACCAGTG CAACTGGAAT    2950

CAGCTGATCA TAGCTATCAA TTACCAGAAA CAGATCAGAC TGTTGTGCGT    3000

ATTAATTTAG GACAAATGGG AGTTGGTGGT GATGATAGTT GGGGACAGCG    3050

AACACACCAA GACTTTACCT TATTTGCAAA TAAAACCTAT CACTATAGCT    3100

TCATGTTGAA TAGTTTAAAC AGA                                 3123
```

SEQ ID NO: 3
(2) INFORMATION FOR SEQ ID NO: 3

(i) SEQUENCE CHARACTERISTICS:
(A) LENGTH: 17 nucleotides
(B) TYPE: nucleic acid
(C) STRANDEDNESS: single
(D) TOPOLOGY: linear (ii) MOLECULE TYPE: synthetic DNA (xi) SEQUENCE DESCRIPTION SEQ ID NO: 3
CCGTCATCCA TATCACC

SEQ ID NO: 4
(2) INFORMATION FOR SEQ ID NO: 4

(i) SEQUENCE CHARACTERISTICS:
(A) LENGTH: 20 nucleotides
(B) TYPE: nucleic acid
(C) STRANDEDNESS: single
(D) TOPOLOGY: linear (ii) MOLECULE TYPE: synthetic DNA (xi) SEQUENCE DESCRIPTION SEQ ID NO: 4
CCTTTGCCCA AGAGCCAACC

SEQ ID NO: 5
(2) INFORMATION FOR SEQ ID NO: 5

(i) SEQUENCE CHARACTERISTICS:
(A) LENGTH: 21 nucleotides
(B) TYPE: nucleic acid
(C) STRANDEDNESS: single
(D) TOPOLOGY: linear (ii) MOLECULE TYPE: synthetic DNA (xi) SEQUENCE DESCRIPTION SEQ ID NO: 5
GCTATTATCA GACTTGGCAC C

SEQ ID NO: 6
(2) INFORMATION FOR SEQ ID NO: 6

(i) SEQUENCE CHARACTERISTICS:
(A) LENGTH: 21 nucleotides
(B) TYPE: nucleic acid

```
(C) STRANDEDNESS: single
(D) TOPOLOGY: linear (ii) MOLECULE TYPE: synthetic DNA (xi) SEQUENCE DESCRIPTION SEQ ID NO: 6
GTAATTCAAT GTTCCAACGT G

SEQ ID NO: 7
(2) INFORMATION FOR SEQ ID NO: 7

(i) SEQUENCE CHARACTERISTICS:

(A) LENGTH: 16 nucleotides
(B) TYPE: nucleic acid
(C) STRANDEDNESS: single
(D) TOPOLOGY: linear (ii) MOLECULE TYPE: synthetic DNA (xi) SEQUENCE DESCRIPTION SEQ ID NO: 7
CGCTTATGGT GTGAAG

SEQ ID NO: 8
(2) INFORMATION FOR SEQ ID NO: 8

(i) SEQUENCE CHARACTERISTICS:
(A) LENGTH: 20 nucleotides
(B) TYPE: nucleic acid
(C) STRANDEDNESS: single
(D) TOPOLOGY: linear (ii) MOLECULE TYPE: synthetic DNA (xi) SEQUENCE DESCRIPTION SEQ ID NO: 8
GGGCTGGCTT AACTATGCGG

SEQ ID NO: 9
(2) INFORMATION FOR SEQ ID NO: 9

(i) SEQUENCE CHARACTERISTICS:
(A) LENGTH: 36 nucleotides
(B) TYPE: nucleic acid
(C) STRANDEDNESS: single
(D) TOPOLOGY: linear (ii) MOLECULE TYPE: synthetic DNA (xi) SEQUENCE DESCRIPTION SEQ ID NO: 9
CTGAATTCGC ATATGGCAAA AAAATTAAAA AAATTC

SEQ ID NO: 10
(2) INFORMATION FOR SEQ ID NO: 10

(i) SEQUENCE CHARACTERISTICS:
(A) LENGTH: 31 nucleotides
(B) TYPE: nucleic acid
(C) STRANDEDNESS: single
(D) TOPOLOGY: linear (ii) MOLECULE TYPE: synthetic DNA (xi) SEQUENCE DESCRIPTION SEQ ID NO: 10
CCAAGCTTAT CTGTTTAAAC TATTCAACAT G

SEQ ID NO: 11
(2) INFORMATION FOR SEQ ID NO: 11

(i) SEQUENCE CHARACTERISTICS:
(A) LENGTH: 36 nucleotides
(B) TYPE: nucleic acid
(C) STRANDEDNESS: single
(D) TOPOLOGY: linear (ii) MOLECULE TYPE: synthetic DNA (xi) SEQUENCE DESCRIPTION SEQ ID NO: 11
GGCCATGGAT CCATGGCAAA AAAATTAAAA AAATTC

SEQ ID NO: 12
(2) INFORMATION FOR SEQ ID NO: 12
```

(i) SEQUENCE CHARACTERISTICS:
(A) LENGTH: 37 nucleotides
(B) TYPE: nucleic acid
(C) STRANDEDNESS: single
(D) TOPOLOGY: linear (ii) MOLECULE TYPE: synthetic DNA (xi) SEQUENCE DESCRIPTION SEQ ID NO: 12
GGCCATCCCG GGTTATCTGT TTAAACTATT CAACATG

---

SEQUENCE LISTING

<160> NUMBER OF SEQ ID NOS: 12

<210> SEQ ID NO 1
<211> LENGTH: 1041
<212> TYPE: PRT
<213> ORGANISM: Alkalilactibacillus ikkense

<400> SEQUENCE: 1

```
Met Ala Lys Lys Leu Lys Lys Phe Asn Tyr Leu Pro Pro Lys Asn Gly
 1               5                  10                  15

Tyr Pro Glu Trp Asn Asn Asn Pro Glu Ile Phe Gln Leu Asn Arg Arg
            20                  25                  30

Glu Ala His Ala Thr Leu Val Pro Tyr Ser Asn Leu Glu Leu Ala Leu
        35                  40                  45

Lys Gly Glu Arg Thr Ala Ser Ser Phe Tyr Gln Ser Leu Asn Gly Ser
    50                  55                  60

Trp Gln Phe Ala Phe Ala Gln Glu Pro Thr Lys Arg Val Ile Asp Phe
65                  70                  75                  80

Tyr Arg Lys Asp Phe Asp His Arg Asp Trp Asp Ser Ile Lys Val Pro
                85                  90                  95

Ser His Trp Gln Leu Glu Gly Tyr Asp Tyr Pro Gln Tyr Thr Asn Thr
            100                 105                 110

Thr Tyr Pro Trp Val Glu Lys Glu Thr Ile Lys Pro Pro Phe Ala Pro
        115                 120                 125

Thr Asn Tyr Asn Pro Val Gly Gln Tyr Val Arg Thr Phe Glu Leu Pro
    130                 135                 140

Thr Asp Trp Asn Gly Ala Pro Val Tyr Leu Asn Phe Gln Gly Val Glu
145                 150                 155                 160

Ser Ala Phe Tyr Val Trp Ile Asn Gly Asp Leu Val Gly Tyr Ser Glu
                165                 170                 175

Asp Thr Phe Thr Pro Ala Glu Phe Asp Ile Thr Pro Tyr Leu Ile Glu
            180                 185                 190

Gly Glu Asn Lys Leu Ala Val Glu Val Tyr Arg Trp Ser Asp Ala Ser
        195                 200                 205

Trp Leu Glu Asp Gln Asp Phe Trp Arg Leu Ser Gly Ile Phe Arg Asp
    210                 215                 220

Val Tyr Leu Tyr Ala Thr Pro Ala Gln His Ile Asp Asp Phe Phe Val
225                 230                 235                 240

Thr His Glu Leu Asp Ala Asp Tyr Arg Asn Ala Thr Leu Lys Ile Asp
                245                 250                 255

Met Lys Val Arg Asp Tyr Phe Glu Ile Gly Glu Pro Val Thr Val Asn
            260                 265                 270

Ala Met Leu Phe Asp Leu Asn Gly Asn Pro Val Leu Lys Gln Pro Leu
        275                 280                 285
```

-continued

```
Leu Ser Ala Val Asp Phe Ser Gly Lys Glu Val Ala Asp Val Ser Val
    290                 295                 300
Ile Thr Thr Ile Asp Asn Pro Leu Lys Trp Ser Ala Glu Asp Pro Asn
305                 310                 315                 320
Leu Tyr Thr Leu Val Leu Ser Leu Val Asp Gln Asn Gly Lys Leu Leu
                325                 330                 335
Glu Thr Glu Ser Cys Arg Val Gly Phe Arg Lys Phe Glu Arg Lys Asp
            340                 345                 350
Gly Leu Met Gln Ile Asn Gly Lys Arg Ile Val Phe Lys Gly Thr Asn
        355                 360                 365
Arg His Glu Phe Ala Ser Asp Lys Gly Arg Ala Ile Thr Ile Asp Asp
    370                 375                 380
Met Val Asn Asp Ile Gln Leu Met Lys Gln His Asn Ile Asn Ala Val
385                 390                 395                 400
Arg Thr Ser His Tyr Pro Asn His Pro Leu Trp Tyr Glu Leu Cys Asp
                405                 410                 415
Thr Tyr Gly Leu Tyr Val Ile Asp Glu Thr Asn Leu Glu Thr His Gly
            420                 425                 430
Thr Trp Val Tyr Gly Gln Lys Gly Leu Ala Glu Thr Ile Pro Gly Ser
        435                 440                 445
Leu Pro Lys Trp Thr Glu Asn Val Leu Asp Arg Cys Asn Ser Met Phe
    450                 455                 460
Gln Arg Asp Lys Asn His Pro Ser Ile Leu Asp Trp Ser Leu Gly Asn
465                 470                 475                 480
Glu Ser Phe Gly Gly Asp Asn Phe Leu Lys Met His Asp Phe Phe Thr
                485                 490                 495
Glu Gln Asp Pro Ala Arg Leu Val His Tyr Glu Gly Ile Phe His Tyr
            500                 505                 510
Arg Glu Ser Glu Arg Ala Ser Asp Met Glu Ser Thr Met Tyr Ile Ser
        515                 520                 525
Pro Glu Gly Ile Glu Asp Tyr Ala Lys Lys Ala Thr Lys Glu Thr Lys
    530                 535                 540
Pro Tyr Ile Leu Cys Glu Phe Ser His Ala Met Gly Asn Ser Leu Gly
545                 550                 555                 560
Asn Phe Tyr Lys Tyr Thr Glu Leu Phe Asp Gln Tyr Pro Ile Leu Gln
                565                 570                 575
Gly Gly Phe Ile Trp Asp Trp Lys Asp Gln Ser Leu Leu Thr Lys Thr
            580                 585                 590
Ala Gly Gly Thr Pro Tyr Leu Ala Tyr Gly Gly Asp Phe Gly Glu Ser
        595                 600                 605
Pro His Asp Gly Asn Phe Ala Gly Asn Gly Leu Ile Phe Gly Asp Gly
    610                 615                 620
Lys Val Ser Pro Lys Ile Phe Glu Val Lys Arg Cys Tyr Gln Asn Val
625                 630                 635                 640
Asp Phe Lys Ala Ile Asp Leu Val His Gly Gln Ile Glu Leu Thr Asn
                645                 650                 655
Lys Tyr Leu Phe Thr Asn Leu Ala Asp Tyr Gln Leu Asn Trp Val Ile
            660                 665                 670
Thr Arg Asn Gly Asp Ala Ile Glu Ser Gly Ala Thr Asn Ile Asn Val
        675                 680                 685
Leu Pro Gly Glu Lys Arg Glu Val Ile Leu Asp Tyr Thr Phe Pro Thr
    690                 695                 700
Gly Val Cys Met Thr Asp Glu Tyr Ile Leu Thr Leu Arg Phe Ser Glu
```

```
                705                 710                 715                 720
Lys Gly Asp Arg Leu Trp Cys Glu Ala Gly His Glu Val Ala Phe Asn
                    725                 730                 735
Gln Phe Val Leu Pro Thr Lys Val Thr Lys Leu Arg Glu Lys Thr Gln
                    740                 745                 750
Asp Thr Lys Thr Leu Ser Val Glu Val Met Gln Asp Arg Leu Val Thr
                    755                 760                 765
Ser Gly Ala Gly Phe Ser Val Gly Phe Asp Thr Lys Ser Gly Met Leu
                    770                 775                 780
Val Ser Tyr Gln Val Gly Gly Asn Glu Leu Val Lys Glu Ala Leu Val
785                 790                 795                 800
Pro Asn Phe Trp Arg Ala Met Thr Asp Asn Asp Arg Gly Asn Gly Leu
                    805                 810                 815
Asp Gln Arg Ser Gln Ile Trp Arg Asp Ala Asn Glu Val Arg Glu Leu
                    820                 825                 830
Val Ser Phe Gln Tyr Glu Val Leu Thr Asn Arg Val Ser Ile Ser Thr
                    835                 840                 845
Val Phe Leu Tyr Glu Asp Leu Asn His Ser Arg Val Glu Leu Asn Phe
850                 855                 860
Leu Ile Thr Gly Thr Gly Glu Ile Lys Val Asp Tyr Val Leu Lys Pro
865                 870                 875                 880
Gly Glu Asp Leu Pro Glu Ile Pro Glu Ile Gly Leu Met Leu Thr Met
                    885                 890                 895
Pro Lys Ser Phe Asp Gln Leu Ser Trp Tyr Gly Lys Gly Pro His Glu
                    900                 905                 910
Ser Tyr Trp Asp Lys Gln Lys Gly Ala Lys Ile Gly Leu Tyr Gln Gly
                    915                 920                 925
Phe Val Gly Asp Gln Tyr Val Pro Tyr Leu Lys Pro Gln Glu Cys Gly
                    930                 935                 940
Asn Lys Val Gly Val Arg Ser Ala Glu Leu Val Asn Asp Val Gly Val
945                 950                 955                 960
Gly Leu Ile Ile Ser Gly Leu Pro Thr Leu Glu Leu Asn Val Leu Pro
                    965                 970                 975
Tyr Thr Pro Val Gln Leu Glu Ser Ala Asp His Ser Tyr Gln Leu Pro
                    980                 985                 990
Glu Thr Asp Gln Thr Val Val Arg Ile Asn Leu Gly Gln Met Gly Val
                    995                 1000                1005
Gly Gly Asp Asp Ser Trp Gly Gln Arg Thr His Gln Asp Phe Thr
                    1010                1015                1020
Leu Phe Ala Asn Lys Thr Tyr His Tyr Ser Phe Met Leu Asn Ser
                    1025                1030                1035
Leu Asn Arg
    1040

<210> SEQ ID NO 2
<211> LENGTH: 3123
<212> TYPE: DNA
<213> ORGANISM: Alkalilactibacillus ikkense

<400> SEQUENCE: 2
atggcaaaaa aattaaaaaa attcaactac ctcccaccaa aaacgggta cccagagtgg      60 aataataatc cggaaatttt tcaacttaat cgaagagagg cgcatgcaac attggtgcca     120
tattctaatt tggaattggc acttaaaggg gagcggacga catcatcatt ttatcaatct     180
ttaaatggta gttggcagtt tgcctttgcc caagagccaa ccaagcgagt gatagatttt     240
```

```
tatcggaaag attttgatca tcgcgattgg gattcgatta aagtaccaag tcattggcag     300
ttagaaggct atgactaccc gcaatacacc aacacaacgt acccatgggt agaaaaagaa     360
acgattaaac ctccatttgc accaacaaat tataatccag tcggacaata tgttcgcacg     420
tttgaattac cgactgattg gaatggagct cccgtttatc tgaatttcca aggtgttgaa     480
tcagctttct acgtctggat aaatggtgat ttggtcggat acagtgagga cactttcaca     540
ccagctgaat ttgatataac tccctattta atagagggtg aaaataagct agcggtagaa     600
gtctatcgtt ggagtgatgc gagctggctt gaagaccagg atttctggag gttaagcggg     660 attttcgtg acgtctatct atatgcaaca ccagctcagc acattgatga tttctttgtc       720
acacacgaac ttgatgcaga ctatcgaaat gcaacgttga agattgatat gaaagtgcgc     780
gattatttcg agattggcga gcctgtcaca gttaatgcga tgctctttga tcttaatggg     840
aatccggttc tcaagcaacc gcttttatcg gcagtagatt tttcaggtaa agaagttgct     900
gatgtgagcg taataacaac aattgataat ccattgaaat ggagtgcgga agatcccaat     960
ctgtacactt tggttttaag tttagttgat cagaatggca agttgcttga aacagaaagc    1020
tgtcgcgttg gatttcgtaa atttgaacgc aaggacggat tgatgcaaat taatggaaag    1080
cggattgtct ttaaagggac aaatcgtcac gaattcgctt ctgataaagg tcgggcgata    1140
acgatagatg atatggttaa tgatattcag ctgatgaagc agcataacat taatgccgtt    1200
cgaacctcac attatccgaa tcatccgctt tggtatgagt tgtgtgatac gtatgggtta    1260
tatgtgattg acgagacaaa cttagagacg cacgggacat gggtttatgg tcaaaaagga    1320
ttggctgaga caataccagg tagtctacca aagtggactg aaaacgtctt ggatcgttgt    1380
aattcaatgt tccaacgtga taaaaaccac ccatcgattc tggattggtc acttggtaat    1440
gaatcttttg gtggcgataa cttcttgaag atgcatgact tctttacgga acaagatcca    1500
gctcgtctgg tgcactatga ggggattttt cattatcgtg aatctgaacg ggcatctgat    1560
atggagagta ccatgtatat ttcgccagaa ggcattgagg actatgcaaa gaaagcgacc    1620
aaggagacga aaccatatat tttatgcgaa ttcagccatg cgatgggcaa ctcgctagga    1680 aactttata agtataccga gctatttgat caatatccga tcttacaagg aggcttcatt      1740
tgggattgga aggatcaatc gctgctaacg aagacagcag gaggcacacc gtatcttgct    1800
tatggtggtg attttggtga atcgccacac gacggcaact tgctggtaa tggtttgatt      1860 tttggagatg gcaaggttag cccgaagatt tttgaagtga agcgttgtta ccaaaatgtt    1920
gatttcaaag caatagactt agtgcacgga caaatcgaat tgaccaataa atacttgttc    1980
accaatctcg ctgactacca actaaattgg gttatcactc gaaacggtga tgcaatagag    2040
tcgggtgcta ctaacatcaa tgtcttacca ggtgaaaaaa gagaggttat acttgactac    2100
acgttcccaa caggcgtttg catgacggat gaatatattt tgacccttcg tttttctgag    2160
aaaggtgatc gcttatggtg tgaagcggga catgaagttg catttaatca gtttgtttta    2220
ccaacaaaag ttacgaaatt acgtgagaag acacaagata ccaagacgct ttcagttgaa    2280
gtaatgcaag atcgacttgt tacatctggt gctggattta gcgtcggatt tgacactaaa    2340
tcgggtatgc ttgttttctta ccaagttgga ggtaatgaat tggtgaaaga ggcacttgtg    2400
ccaaacttct ggcgtgcaat gactgataat gatcgcggga acggactcga tcaacggagt    2460
cagatttggc gtgatgcaaa tgaggtacgt gaattggttt catttcagta tgaagtgttg    2520
accaatagag taagcatatc aacggttttc ttatatgaag acctcaacca ttcacgcgtt    2580
gaacttaact ttttgattac tggaactggt gaaataaagg tggattatgt actgaaaccg    2640
```

-continued

```
ggagaagatt taccagaaat accagagata ggtttgatgt taacgatgcc taagtcgttt    2700
gatcagttaa gttggtatgg aaaaggccca catgaatcgt attgggataa acaaaaaggc    2760
gcgaaaatag gtctttatca aggatttgtc ggcgatcagt atgtgccgta tttgaaacca    2820
caagaatgtg gcaacaaagt aggagttcgt tcagcagaat tggttaatga tgttggtgtt    2880
ggtttgatta taagtggact tccaacgctg gagttaaatg tcttaccata cacaccagtg    2940
caactggaat cagctgatca tagctatcaa ttaccagaaa cagatcagac tgttgtgcgt    3000
attaatttag gacaaatggg agttggtggt gatgatagtt ggggacagcg aacacaccaa    3060
gactttacct tatttgcaaa taaaacctat cactatagct tcatgttgaa tagtttaaac    3120
aga                                                                    3123
```

<210> SEQ ID NO 3
<211> LENGTH: 17
<212> TYPE: DNA
<213> ORGANISM: Artificial sequence
<220> FEATURE:
<223> OTHER INFORMATION: Synthetic custom-made primer

<400> SEQUENCE: 3
ccgtcatcca tatcacc                                                     17

<210> SEQ ID NO 4
<211> LENGTH: 20
<212> TYPE: DNA
<213> ORGANISM: Artificial sequence
<220> FEATURE:
<223> OTHER INFORMATION: Synthetic custom-made primer

<400> SEQUENCE: 4
cctttgccca agagccaacc                                                  20

<210> SEQ ID NO 5
<211> LENGTH: 21
<212> TYPE: DNA
<213> ORGANISM: Artificial sequence
<220> FEATURE:
<223> OTHER INFORMATION: Synthetic custom-made primer

<400> SEQUENCE: 5
gctattatca gacttggcac c                                                21

<210> SEQ ID NO 6
<211> LENGTH: 21
<212> TYPE: DNA
<213> ORGANISM: Artificial sequence
<220> FEATURE:
<223> OTHER INFORMATION: Synthetic custom-made primer

<400> SEQUENCE: 6
gtaattcaat gttccaacgt g                                                21

<210> SEQ ID NO 7
<211> LENGTH: 16
<212> TYPE: DNA
<213> ORGANISM: Artificial sequence
<220> FEATURE:
<223> OTHER INFORMATION: Synthetic custom-made primer

<400> SEQUENCE: 7
cgcttatggt gtgaag                                                      16

```
<210> SEQ ID NO 8
<211> LENGTH: 20
<212> TYPE: DNA
<213> ORGANISM: Artificial sequence
<220> FEATURE:
<223> OTHER INFORMATION: Synthetic custom-made primer

<400> SEQUENCE: 8
gggctggctt aactatgcgg                                               20

<210> SEQ ID NO 9
<211> LENGTH: 36
<212> TYPE: DNA
<213> ORGANISM: Artificial sequence
<220> FEATURE:
<223> OTHER INFORMATION: Synthetic custom-made primer

<400> SEQUENCE: 9
ctgaattcgc atatggcaaa aaaattaaaa aaattc                             36

<210> SEQ ID NO 10
<211> LENGTH: 31
<212> TYPE: DNA
<213> ORGANISM: Artificial sequence
<220> FEATURE:
<223> OTHER INFORMATION: Synthetic custom-made primer

<400> SEQUENCE: 10
ccaagcttat ctgtttaaac tattcaacat g                                  31

<210> SEQ ID NO 11
<211> LENGTH: 36
<212> TYPE: DNA
<213> ORGANISM: Artificial sequence
<220> FEATURE:
<223> OTHER INFORMATION: Synthetic custom-made primer

<400> SEQUENCE: 11
ggccatggat ccatggcaaa aaaattaaaa aaattc                             36

<210> SEQ ID NO 12
<211> LENGTH: 37
<212> TYPE: DNA
<213> ORGANISM: Artificial sequence
<220> FEATURE:
<223> OTHER INFORMATION: Synthetic custom-made primer

<400> SEQUENCE: 12
ggccatcccg ggttatctgt ttaaactatt caacatg                            37
```

The invention claimed is:

1. A purified cold-active beta-galactosidase having the amino acid sequence as defined in SEQ ID NO. 1 or one having at least 90% homology to the amino acid sequence as defined in SEQ ID NO. 1, the amino acid sequence being selected so that the enzyme has a stable enzymatic activity at temperatures less than 8° C.

2. A beta-galactosidase according to claim 1, wherein the amino acid sequence has at least 95%, homology to the amino acid sequence as defined in SEQ ID NO. 1.

3. A beta-galactosidase according to claim 1, wherein it is produced by a strain of an *Alkalilactibacillus*.

4. A beta-galactosidase according to claim 1, wherein it is produced by *Alkalilactibacillus ikkense*.

5. An isolated DNA sequence comprising a gene which encodes the beta-galactosidase according to claim 1.

6. An isolated DNA sequence, which a) encodes a protein with an amino acid sequence as given in SEQ ID NO. 2, or b) hybridizes to the sequence of a), at 6×SSC, 0.5% SDS and 50% formamide at 42° C., before being washed in a solution of 0.1% ×SSC, 0.5% SDS at 68° C., or c) is degenerative of the sequence of a) or b).

7. A DNA sequence according to claim 6, wherein the sequence is as given in SEQ ID NO. 2.

8. A recombinant vector comprising a DNA sequence of claim 5.

9. A vector of claim 8, wherein said vector is an expression vector.

10. A host cell transformed with a vector of claim 8.

11. A cell according to claim 10, wherein the cell is selected from the group consisting of *Escherichia, Bacillus, Bifidobacterium, Lactococcus, Lactobacillus, Streptomyces, Leu-*

*conostoc, Streptomyces, Saccharomyces, Kluyveromyces, Candida, Torula, Torulopsis* and *Aspergillus*.

12. A cell of claim 11, wherein the cell is selected from the group consisting of *Bifidobacterium breve, Bifidobacterium longum, Bifidobacteriuminfantis, Bifidobacterium bifidum, Bifidobacterium animalis*, and *Lactococcus lactis*.

13. Use of a cell of claim 10 for producing a product selected from the group consisting of lactose-free milk, low-lactose milk, yoghurt, cheese, fermented milk products, dietary supplement and probiotic comestible product comprising adding the host cell of claim 10.

14. A method according to claim 13 for producing a dairy product with a lactose concentration at 1% w/v or lower.

15. A method according to claim 14, wherein the lactose concentration is 0.1% w/v or lower.

16. A method according to claim 15, wherein the lactose concentration is 0.01% w/v or lower.

17. A method of a beta-galactosidase according to claim 1 for producing a product selected from the group consisting of lactose-free milk, low-lactose milk, yoghurt, cheese, fermented milk products, dietary supplement and probiotic comestible product comprising adding the beta-galactosiadase of claim 1.

18. A method according to claim 17 for producing a dairy product with a lactose concentration at 1% w/v or lower.

19. A method according to claim 18, wherein the lactose concentration is 0.1% w/v or lower.

20. A method according to claim 19, wherein the lactose concentration is 0.01% w/v or lower.

21. A process for producing an enzyme of claim 1, comprising culturing a cell of any one of claims 10 to 12 in a suitable culture medium under conditions permitting expression of said enzyme, and recovering the resulting enzyme from the culture.

22. A process according to claim 21, wherein the resulting enzyme is immobilized.

23. A psychrophilic bacterium *Alkalilactibacillus ikkense* BCCM Accession No LMG P-24866 and variants and mutants derived therefrom capable of producing a cold-active beta galactosidase defined by claim 1.

* * * * *